US009464141B2

(12) United States Patent
Asundi et al.

(10) Patent No.: US 9,464,141 B2
(45) Date of Patent: Oct. 11, 2016

(54) ANTI-ETBR ANTIBODIES AND IMMUNOCONJUGATES

(71) Applicant: Genentech, Inc., South San Francisco, CA (US)

(72) Inventors: Jyoti Asundi, Foster City, CA (US); Suzanna Clark, Pacificia, CA (US); Paul Polakis, Mill Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/418,314

(22) PCT Filed: Aug. 1, 2013

(86) PCT No.: PCT/US2013/053248
§ 371 (c)(1),
(2) Date: Jan. 29, 2015

(87) PCT Pub. No.: WO2014/022679
PCT Pub. Date: Feb. 6, 2014

(65) Prior Publication Data
US 2015/0183883 A1 Jul. 2, 2015

Related U.S. Application Data

(60) Provisional application No. 61/678,916, filed on Aug. 2, 2012.

(51) Int. Cl.
*A61K 39/395* (2006.01)
*C07K 16/30* (2006.01)
*C07K 16/28* (2006.01)
*A61K 47/48* (2006.01)
*A61K 31/551* (2006.01)
*A61K 45/06* (2006.01)
*A61K 39/00* (2006.01)

(52) U.S. Cl.
CPC ......... *C07K 16/3053* (2013.01); *A61K 31/551* (2013.01); *A61K 45/06* (2013.01); *A61K 47/48384* (2013.01); *A61K 47/48407* (2013.01); *A61K 47/48561* (2013.01); *A61K 47/48623* (2013.01); *A61K 47/48715* (2013.01); *C07K 16/2869* (2013.01); *A61K 2039/505* (2013.01); *C07K 2317/24* (2013.01); *C07K 2317/56* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,773,223 A | 6/1998 | Shyamala et al. | |
| 6,214,345 B1 | 4/2001 | Firestone et al. | |
| 6,313,276 B1 | 11/2001 | Imura et al. | |
| 7,049,311 B1 | 5/2006 | Thurston et al. | |
| 7,067,511 B2 | 6/2006 | Thurston et al. | |
| 7,265,105 B2 | 9/2007 | Thurston et al. | |
| 7,303,749 B1 | 12/2007 | Chari et al. | |
| 7,498,298 B2 | 3/2009 | Doronina et al. | |
| 7,521,541 B2 | 4/2009 | Eigenbrot et al. | |
| 7,528,126 B2 | 5/2009 | Howard et al. | |
| 7,557,099 B2 | 7/2009 | Howard et al. | |
| 7,601,354 B2 | 10/2009 | Chari et al. | |
| 7,659,241 B2 | 2/2010 | Senter et al. | |
| 7,745,394 B2 | 6/2010 | Doronina et al. | |
| 7,750,116 B1 * | 7/2010 | Doronina ......... | A61K 47/48407 530/330 |
| 7,829,531 B2 | 11/2010 | Senter et al. | |
| 7,851,437 B2 | 12/2010 | Senter et al. | |
| 7,855,275 B2 | 12/2010 | Eigenbrot et al. | |
| 7,964,566 B2 | 6/2011 | Doronina et al. | |
| 7,964,567 B2 | 6/2011 | Doronina et al. | |
| 7,994,135 B2 | 8/2011 | Doronina et al. | |
| 8,088,387 B2 | 1/2012 | Steeves et al. | |
| 8,142,784 B2 | 3/2012 | Ebens et al. | |
| 8,198,417 B2 | 6/2012 | Steeves et al. | |
| 8,309,300 B2 | 11/2012 | Junutula et al. | |
| 8,557,780 B2 | 10/2013 | Doronina et al. | |
| 9,056,910 B2 * | 6/2015 | Chen ................ | A61K 39/39558 |
| 2006/0094676 A1 | 5/2006 | Lahav | |
| 2007/0269442 A1 | 11/2007 | Webber | |
| 2008/0075712 A1 | 3/2008 | Hattori | |
| 2009/0036431 A1 | 2/2009 | Gauzy et al. | |
| 2009/0226925 A1 | 9/2009 | Grebe et al. | |
| 2009/0304710 A1 | 12/2009 | Park et al. | |
| 2010/0003240 A1 | 1/2010 | Schneider et al. | |
| 2010/0047257 A1 | 2/2010 | Blanc et al. | |
| 2010/0249096 A1 | 9/2010 | Aay et al. | |
| 2011/0086837 A1 | 4/2011 | Belvin et al. | |

(Continued)

FOREIGN PATENT DOCUMENTS

EP 522868 A1 1/1993
WO 00/67024 A1 11/2000

(Continued)

OTHER PUBLICATIONS

Allard et al DNA and Cell Biology vol. 30(9) p. 727 (2011).*

(Continued)

*Primary Examiner* — Sheela J Huff
(74) *Attorney, Agent, or Firm* — McNeill Baur PLLC

(57) ABSTRACT

The invention provides anti-ETBR antibodies and immunoconjugates and methods of using the same. In some embodiments, an immunoconjugate comprising an antibody that binds ETBR covalently attached to a cytotoxic agent is provided, wherein the antibody binds an epitope within amino acids 64 to 101 of SEQ ID NO: 10. In some embodiments, the cytotoxic agent is a pyrrolobenzodiazepine.

30 Claims, 6 Drawing Sheets

(56) References Cited

U.S. PATENT DOCUMENTS

| | | | |
|---|---|---|---|
| 2011/0105521 A1 | 5/2011 | Garcia-Echeverria et al. | |
| 2011/0206702 A1* | 8/2011 | Polakis | A61K 47/48384 424/174.1 |
| 2011/0256157 A1* | 10/2011 | Howard | A61K 47/48561 424/181.1 |
| 2012/0148610 A1 | 6/2012 | Doronina et al. | |
| 2013/0028917 A1 | 1/2013 | Howard et al. | |
| 2013/0266595 A1* | 10/2013 | Flygare | A61K 47/48384 424/181.1 |
| 2013/0295007 A1 | 11/2013 | Chen et al. | |
| 2014/0120118 A1* | 5/2014 | Howard | A61K 47/48384 424/178.1 |
| 2014/0127239 A1* | 5/2014 | Howard | A61K 47/48338 424/181.1 |
| 2015/0209444 A1* | 7/2015 | Chari | A61K 47/48384 424/181.1 |

FOREIGN PATENT DOCUMENTS

| | | |
|---|---|---|
| WO | 01/00198 | 1/2001 |
| WO | 01/98351 A2 | 12/2001 |
| WO | 02/61087 A2 | 8/2002 |
| WO | 03/016494 A2 | 2/2003 |
| WO | 03/025138 A2 | 3/2003 |
| WO | 2004/048938 A2 | 6/2004 |
| WO | 2005/081711 A2 | 9/2005 |
| WO | 2005/082023 | 9/2005 |
| WO | 2005/095972 | 10/2005 |
| WO | 2005/117986 A2 | 12/2005 |
| WO | 2006/034488 A2 | 3/2006 |
| WO | 2006/034488 A3 | 3/2006 |
| WO | 2006/060533 | 6/2006 |
| WO | 2007/064345 | 6/2007 |
| WO | 2007/100385 | 9/2007 |
| WO | 2009/012256 A1 | 1/2009 |
| WO | 2009/016516 A2 | 2/2009 |
| WO | 2010/009124 | 1/2010 |
| WO | 2010/099273 | 9/2010 |
| WO | 2011/056983 | 5/2011 |
| WO | 2011/106297 | 9/2011 |
| WO | 2011/130598 | 10/2011 |
| WO | 2011/156328 | 12/2011 |
| WO | 2012045776 * | 4/2012 |
| WO | 2012/074757 | 6/2012 |
| WO | 2013/055987 | 4/2013 |
| WO | 2014/159981 A2 | 10/2014 |

OTHER PUBLICATIONS

Yamaguchi et al Biotechnology Letters vol. 26 p. 293 (2004)].*
English translation of WO 2012045776, 62 pages (2012).*
Asundi et al Clinical Cancer Research vol. 17 p. 965 (published online on Jan. 18, 2011).*
(Written Opinion for PCT/US2011/025642), (2011).
International Search Report and Written Opinion for PCT App. No. PCT/US2013/053248, mailed Jan. 10, 2014 (11 pages).
Adair et al., "Antibody-drug conjugates—a perfect synergy" Expert Opin Biol Therapy 12(9): 1191-1206 ( 2012).
Antonow et al., "Structure-Activity Relationships of Monomeric C2-Aryl Pyrrolo[2,1-c][1,4]benzodiazepine (PBD) Antitumor Agents" J Med Chem(53):2927-2941 (2010).
Arai et al., "Cloning and Expression of a cDNA Encoding an Endothelin Receptor" Nature 348(20):730-732 (1990).
Asundi et al., "An Antibody-Drug Conjugate Targeting the Endothelin B Receptor for the Treatment of Melanoma" Clinical Cancer Research, the American Association for Cancer Research 17(5):965-975 (Mar. 1, 2011).
Asundi et al., "MAPK Pathway Inhibition Enhances the Efficacy of an Anti-Endothelin B Receptor Drug Conjugates by Inducing Target Expression in Melanoma" Molecular Cancer Therapeutics 13(6):1599-1610 (Jun. 2014).
Bagnato et al., "Endothelin Receptor Blockade Inhibits Proliferation of Kaposi's Sarcoma Cells" The American Journal of Pathology 158(3):841-847 (Mar. 2001).
Battistini et al., "Growth Regulatory Properties of Endothelins" Peptides 14:385-399 (1993).
Brown et al., "Transforming Growth Factor-β: Role in Mediating Serum-Induced Endothelin Production by Vascular Endothelial Cells" Endocrinology 129(5):2355-2359 (1991).
Casset et al., Biochem. Biophys. Res. Commun. (Examiner cited), 307(1):198-205 ( 2003).
Chari et al., "Immunoconjugates containing novel maytansinoids: Promising anticancer drugs" Cancer Res 52:127-131 ( 1992).
Chen et al., "Selection and analysis of an optimized anti-VEGF antibody: crystal structure of an affinity-matured Fab in complex with antigen" J Mol Biol. 293(4):865-81 ( 1999).
De Pascalis et al., "Grafting of 'abbreviated' complementarity-determining regions containing specificity-determining residues essential for ligand contact to engineer a less immunogenic humanized monoclonal antibody" J Immunol 169:3076-3084 ( 2002).
Demunter et al., "Expression of the endothelin-B receptor in pigment cell lesions of the skin: evidence for its role as tumor progession marker in malignant melanoma" Virchows Archiv ;438(5):485-491 (May 1, 2001).
Doppalapudi et al., "Chemically programmed antibodies: endothelin receptor targeting covX-bodies" Biorg and Med Chem Lett 17(2):501-506 ( 2007).
Elshourbagy et al., "Molecular Characterization and Regulation of the Human Endothelin Receptors" Journal of Biological Chemistry 268(6):3873-3879 (Feb. 25, 1993).
Flygare et al., "Antibody-drug Conjugates for the Treatment of Cancer" Chem Biol Drug Des 81:113-121 ( 2013).
Grantcharova et al., "The Extracellular N Terminus of the Endothelin B (ETb) Receptor is Cleaved by a Metalloprotease in an Agonist-dependent Process" J Biol Chem 277(46):43933-43941 (Nov. 15, 2002).
Hardwick et al., "Identification of Biomarkers for Tumor Endothelial Cell Proliferation through Gene Expression Profiling" Molecular Cancer Therapeutics 4(3):413-425 (Mar. 2005).
Hartley et al., "SG2285, a novel C2-aryl-substituted pyrrolobenzodiazepine dimer prodrug that cross-links DNA and exerts highly potent antitumor activity" Cancer Res. 70(17):6849-6858 (2010).
Hilal-Dandan et al., "Coupling of the Type A Endothelin Receptor to Multiple Responses in Adult Rat Cardiac Myocytes" Molecular Pharmacology 45:1183-1190 (1994).
Hosoda et al., "Cloning and expression of human endothelin-1 receptor cDNA" FEBS Letter 287(1,2):23-26 (Aug. 1991).
Ihara et al., "An Endothlin Receptor ($ET_A$) Antagonist Isolated From Streptomyces Misakiensis" Biochemical and Biophysical Research Communications 178(1):132-137 (Jul. 15, 1991).
Ihara et al., "Biological Profiles of Highly Potent Novel Endothelin Antagonists Selective or the ET$_{subscript:A}$ Receptor" Life Sciences 50:247-255 (1992).
Inoue et al., "The Human Endothelin Family: Three Structurally and Pharmacologically Distinct Isopeptides Predicted by Three Separate Genes" Proc. Natl. Acad. Sci, USA 86:2863-2867 (Apr. 1989).
Ito et al., "Endothelin $ET_A$ Receptor Antagonist Blocks Cardiac Hypertrophy Provoked by Hemodynamic Overload" Circulation 89(5):2198-2203 (May 1994).
Ito et al., "Endothelin-1 Induces Hypertrophy With Enhanced Expression of Muscle-Specific Genes in Cultured Neonatal Rat Cardiomyocytes" Circulation Research 69(1):209-215 (Jul. 1991).
Jeffrey et al., "A Potent Anti-CD70 Antibody—Drug Conjugate Combining a Dimeric Pyrrolobenzodiazepine Drug with Site-Specific Conjugation Technology" Bioconjugate Chemistry 24:1256-1263 ( 2013).
Jones et al., "Endothelin Stimulates Multiple Responses in Isolated Adult Ventricular Cardiac Myocytes" American Journal of Physiology 263(32):H1447-H1454 (1992).
King et al., "Phenylephrine, endothelin, prostaglandin $F_{2\alpha}$, and leukemia inhibitory factor induce different cardiac hypertrophy phenotypes in vitro" Endocrine 9(1):45-55 (Aug. 1998).

(56) References Cited

OTHER PUBLICATIONS

Lahav et al., "An Endothelin Receptor B Antagonist Inhibits Growth and Induces Cell Death in Human Melanoma Cells in Vitro and in Vivo" Proceedings of the National Academy of Sciences of the United States, National Academy of Science 96(20):11496-11500 (Sep. 1, 1999).

Lamminmaki et al., "Crystal structure of a recombinant anti-estradiol Fab fragment in complex with 17β-estradiol" Journal of Biological Chemistry 276(39):36687-36694 (Sep. 28, 2001).

MacCallum et al., "Antibody-antigen interactions: contact analysis and binding site topography" J Mol Biol. 262(5):732-45 ( 1996).

Nakamuta et al. et al., "Cloning and sequence analysis of a cDNA encoding human non-selective type of endothelin receptor" Biochem Bioph Res CO 177(1):34-9 ( 1991).

Ogawa et al. et al., "Jul. 15;178(1):. Molecular cloning of a non-isopeptide-selective human endothelin receptor" Biochem Bioph Res CO 178(1):248-55 ( 1991).

Other Database, EBI Accession No. UNIPROT:P24530, Mar. 1, 1992.

Padlan et al., "Structure of an antibody-antigen complex: crystal structure of the HyHEL-10 Fab-lysozyme complex" Proc. Natl. Acad. Sci. 86:5938-5942 (Aug. 1989).

Rosano et al., "Endothelin-B Receptor Blockade Inhibits Molecular Effectors of Melanoma Cell Progression" Journal of Cardiovascular Pharmacology, Raven Press 44( SUPPL 1):S136-S139 (Nov. 1, 2004).

Rudikoff et al., Proc. Natl. Acad. Sci. USA, Immunology, vol. 79, (1982), pp. 1979-1983, abstract on p. 1979.

Sakamoto et al. et al., "Cloning and Functional Expression of Human cDNA for the $ET_B$ Endothelin Receptor" Biochem Bioph Res CO 178(2):656-663 ( 1991).

Shubeita et al., "Endothelin Induction of Inositol Phospholipid Hydrolysis, Sarcomere Assembly, and Cadiac Gene Expression in Ventricular Myocytes. A paracrine mechanism for myocardial cell hypertrophy" Journal of Biological Chemistry 265(33):20555-20562 (Nov. 25, 1990).

Sullivan et al., "Endothelins in the urinary tract" BJU International 86:97-106 (2000).

Suzuki et al., "Endothelin-1 Stimulates Hypertrophy and Contractility of Neonatal Rat Cardiac Myocytes in a Serum-Free Medium. II" Journal of Cardiovascular Pharmacology 17(7):S182-S186 (1991).

Takizawa et al., "Immunolocalization of Endothelin-B Receptor in Mouse Intestinal Tract" Journal of Cardiovascular Pharmacology 44( SUPPL 1):S329-S331 (Nov. 2004).

Vajdoes et al. et al., "Comprehensive functional maps of the antigen-binding site of an anti-ErbB2 antibody obtained with shotgun scanning mutagenesis" J Mol Biol 320(2):415-428 (Jul. 5, 2002).

Vane et al. et al., "Endothelins come home to roost" Nature 348(6303):673 ( 1990).

Webb et al., "The Endothelin Receptor Antagonist, BQ-123, Inhibits Angiotensin II-induced Contractions in Rabbit Aorta" Biomedical and Biophysical Research Communications 185(3):887-892 (Jun. 30, 1992).

Wei et al., "Endothelin in Human Congestive Heart Failure" Circulation 89(4):1580-1586 (Apr. 1994).

Whitworth et al., "Endothelin in the Kidney in Malignant Phase Hypertension" Hypertension 26:925-931 (Dec. 1995).

Wu et al., "1,25(OH)2 vitamin D3, and retinoic acid antagonize endothelin-stimulated" J. Clin. Invest. 97:1577-1588 (1996).

Wu et al., "Humanization of a Murine Monoclonal Antibody by Simultaneous Optimization of Framework and CDR Residues" J Mol Biol 294:151-162 ( 1999).

Yamaguchi et al., "Characterization and Application of Monoclonal Antibodies Against Human Endothelin B Receptor Expressed in Insect Cells" Biotechnology Letters 26(4):293-299 (Feb. 2004).

Yanagisawa and Masaki, "Molecular Biology and Biochemistry of the Endothelins" Trends Pharm. Sci. 10:374-378 (Sep. 1989).

Yang et al., "RG7204 (PLX4032), a Selective BRAFV600E Inhibitor, Displays Potent Antitumor Activity in Preclinical Melanoma Models" Cancer Research 70(13):5518-5527 (2010).

Yokomori et al., "Enhanced Expression of Endothelin B Receptor at Protein and Gene Levels in Human Cirrhotic Liver" The American Journal of Pathology 159(4):1353-1362 (Oct. 2001).

* cited by examiner

Full-Length Light Chain of Murine 5E9
DVVMTQTPLTLSVTIGQPASISCKSSQSLLDSDGKTYLNWLLQRPGQSPKRLIYLVSKLDSGVPDRFTGSGSGTDF
TLKITRVEAEDLGVYYCWQGTHFPYTFGGGTKLEIKRADAAPTVSIFPPSSEQLTSGGASVVCFLNNFYPKDINVK
WKIDGSERQNGVLNSWTDQDSKDSTYSMSSTLTLTKDEYERHNSYTCEATHKTSTSPIVKSFNRNEC (SEQ ID
NO:1)

VL of Murine 5E9
DVVMTQTPLTLSVTIGQPASISCKSSQSLLDSDGKTYLNWLLQRPGQSPKRLIYLVSKLDSGVPDRFTGSGSGTDF
TLKITRVEAEDLGVYYCWQGTHFPYTFGGGTKLEIK (SEQ ID NO:3)

FIG. 1

Full-Length Heavy Chain of Murine 5E9
QVQLLQSGAELARPGASVKLSCKASGYTFTSYWMQWVKQRPGQGLEWIGTIYPGDGDTSYAQKFKGKATLTTDKYS
STAYMQLSSLASEDSAVYYCARWGYAYDIDNWGQGTTVTVSSASTKGPSVYPLAPVCGDTTGSSVTLGCLVKGYFP
EPVTLTWNSGSLSSGVHTFPAVLQSDLYTLSSSVTVTSSTWPSQSITCNVAHPASSTKVDKKIEPRGPTIKPCPPC
KCPAPNLLGGPSVFIFPPKIKDVLMISLSPIVTCVVVDVSEDDPDVQISWFVNNVEVHTAQTQTHREDYNST
LRVVSALPIQHQDWMSGKEFKCKVNNKDLPAPIERTISKPKGSVRAPQVYVLPPPEEEMTKKQVTLTCMVTDFMPE
DIYVEWTNNGKTELNYKNTEPVLDSDGSYFMYSKLRVEKKNWVERNSYSCSVVHEGLHNHHTTKSFSRTPGK
(SEQ ID NO:2)

VH of Murine 5E9
QVQLLQSGAELARPGASVKLSCKASGYTFTSYWMQWVKQRPGQGLEWIGTIYPGDGDTSYAQKFKGKATLTTDKYS
STAYMQLSSLASEDSAVYYCARWGYAYDIDNWG (SEQ ID NO:4)

FIG. 2

Full-Length Light Chain of hu5E9.v1
DIQMTQSPSSLSASVGDRVTITCKSSQSLLDSDGKTYLNWLQQKPGKAPKRLIYLVSKLDSGVPSRFSGSGSGTDF
TLTISSLQPEDFATYYCWQGTHFPYTFGQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSSPVTKSFNRGEC (SEQ ID
NO:5)

VL of hu5E9.v1
DIQMTQSPSSLSASVGDRVTITCKSSQSLLDSDGKTYLNWLQQKPGKAPKRLIYLVSKLDSGVPSRFSGSGSGTDF
TLTISSLQPEDFATYYCWQGTHFPYTFGQGTKVEIK (SEQ ID NO:7)

FIG. 3

Full-Length Heavy Chain of hu5E9.v1
EVQLVESGGGLVQPGGSLRLSCAASGYTFTSYWMQWVRQAPGKGLEWIGTIYPGDGDTSYAQKFKGRATLSTDKSK
NTAYLQMNSLRAEDTAVYYCARWGYAYDIDNWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQKSLSLSPGK
(SEQ ID NO:6)

VH of hu5E9.v1
EVQLVESGGGLVQPGGSLRLSCAASGYTFTSYWMQWVRQAPGKGLEWIGTIYPGDGDTSYAQKFKGRATLSTDKSK
NTAYLQMNSLRAEDTAVYYCARWGYAYDIDNWG (SEQ ID NO:8)

FIG. 4

VH of hu5E9.v2
EVQLVQSGAEVKKPGASVKVSCKASGYTFTSYWMQWVRQAPGQGLEWIGTIYPGDGDTSYAQKFKGRVTITRDTST
STAYLELSSLRSEDTAVYYCARWGYAYDIDNWG (SEQ ID NO:9)

FIG. 5

MQPPPSLCGRALVALVLACGLSRIWGEERGFPPDRATPLLQTAEIMTPPTKTLWPKGSNASLARSLAPAEVPKGDR
TAGSPPRTISPPPCQGPIEIKETFKYINTVVSCLVFVLGIIGNSTLLRIIYKNKCMRNGPNILIASLALGDLLHIV
IDIPINVYKLLAEDWPFGAEMCKLVPFIQKASVGITVLSLCALSIDRYRAVASWSRIKGIGVPKWTAVEIVLIWVV
SVVLAVPEAIGFDIITMDYKGSYLRICLLHPVQKTAFMQFYKTAKDWWLFSFYFCLPLAITAFFYTLMTCEMLRKK
SGMQIALNDHLKQRREVAKTVFCLVLVFALCWLPLHLSRILKLTLYNQNDPNRCELLSFLLVLDYIGINMASLNSC
INPIALYLVSKRFKNCFKSCLCCWCQSFEEKQSLEEKQSCLKFKANDHGYDNFRSSNKYSSS (SEQ ID
NO:10)

Signal sequence.

amino acids 1-26

Transmembrane domains.

amino acids 101-121, 137-157, 177-197, 216-236, 275-295, 323-343, 362-382

N-glycosylation sites.

amino acids 59-62, 119-122 cAMP- and cGMP-dependent protein kinase phosphorylation site.

amino acids 302-305

Tyrosine kinase phosphorylation site.

amino acids 424-430

N-myristoylation sites.

amino acids 57-62, 115-120, 170-175, 306-311, 371-376

7 transmembrane receptor homology.

amino acids 118-386

*FIG. 6*

A      *IN VIVO* DERIVED
FACS EDNRB (ETBR; target A)
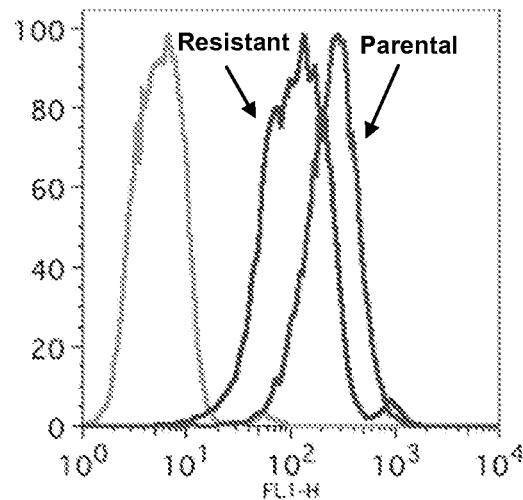
B      *IN VITRO* DERIVED
FACS EDNRB (ETBR; target A)
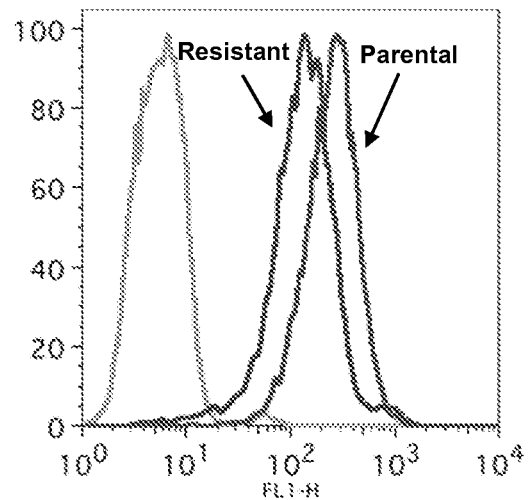
*FIG. 9*

ANTI-ETBR ANTIBODIES AND IMMUNOCONJUGATES

FIELD OF THE INVENTION

The present invention relates to immunoconjugates comprising anti-ETBR antibodies and methods of using the same.

BACKGROUND

Melanoma is an aggressive form of skin cancer that has recently undergone an alarming increase in incidence. Although cures can be achieved with surgical resection of localized lesions, the advanced stages of melanoma are only poorly responsive to currently approved therapies. The 5-year survival rate for stage IV metastatic melanoma is approximately 10%. New therapeutic approaches, including antisense to Bcl2, antibodies to CTLA4, small molecule RAF kinase inhibitors, and adoptive immunotherapy, are currently in clinical testing for metastatic melanoma. The results from some of these recent studies seem to be encouraging, but a durable impact on overall survival will likely require therapeutic combinations including additional new agents.

More than 20 years ago, endothelin-1 (ET-1) was isolated from aortic endothelial cells and found to have potent vasoconstrictive activity. The receptors for endothelins were cloned shortly thereafter and their expression in various cell types, including melanocytes and melanoma cells, pointed to functions independent of their role in endothelium. It is now well recognized that the endothelin B receptor (ETBR, EDNBR) is critical for the faithful derivation of melanocytic cells emanating from the neural crest during embryonic development. Melanocyte precursors rely on ETBR activity to proliferate and migrate from the neural tube to their final destinations. Mice with defective genes coding for either ETBR or endothelin-3 (ET-3) exhibit a pigmentation deficit in their coats and a shortage of enteric ganglion cells, also derived from the neural crest. These characteristics strongly resemble those associated with the WS4 variant of Waardenburg syndrome in humans, which has been attributed to germline mutations in either ET-3 or ETBR. An additional variant of this syndrome, WS2, has been mapped to heritable mutations in the microphthalmia-associated transcription factor (MITF), a key regulator of melanocyte development and a melanoma proto-oncogene.

The strong genetic evidence linking ETBR activity to the fate of melanoblasts underscores a potential role for this receptor in the progression of melanoma. The expression of ETBR mRNA and protein was reported to increase during disease progression from dysplastic nevi to metastatic melanoma. Blockade of ETBR activity by 2 independent small molecule inhibitors interfered with growth and survival of melanoma cells and tumor xenografts. These preclinical studies implicate ETBR as a potential driver of melanoma progression.

There is a need in the art for agents that target ETBR for the diagnosis and treatment of ETBR-associated conditions, such as cancer. The invention fulfills that need and provides other benefits.

SUMMARY

The invention provides anti-ETBR antibodies and immunoconjugates and methods of using the same.

In some embodiments, an immunoconjugate comprising an antibody that binds ETBR covalently attached to a cytotoxic agent is provided, wherein the antibody binds an epitope within amino acids 64 to 101 of SEQ ID NO: 10. In some embodiments, the cytotoxic agent is a pyrrolobenzodiazepine.

In some embodiments, the antibody comprises (i) HVR-H3 comprising the amino acid sequence of SEQ ID NO: 14, (ii) HVR-L3 comprising the amino acid sequence of SEQ ID NO: 17, and (iii) HVR-H2 comprising the amino acid sequence of SEQ ID NO: 13. In some embodiments, the antibody comprises (i) HVR-H1 comprising the amino acid sequence of SEQ ID NO: 12, (ii) HVR-H2 comprising the amino acid sequence of SEQ ID NO: 13, and (iii) HVR-H3 comprising the amino acid sequence of SEQ ID NO: 14. In some embodiments, the antibody comprises (i) HVR-H1 comprising the amino acid sequence of SEQ ID NO: 12, (ii) HVR-H2 comprising the amino acid sequence of SEQ ID NO: 13, (iii) HVR-H3 comprising the amino acid sequence of SEQ ID NO: 14, (iv) HVR-L1 comprising the amino acid sequence of SEQ ID NO: 15, (v) HVR-L2 comprising the amino acid sequence of SEQ ID NO: 16, and (vi) HVR-L3 comprising the amino acid sequence of SEQ ID NO: 17. In some embodiments, the antibody comprises (i) HVR-L1 comprising the amino acid sequence of SEQ ID NO: 15, (ii) HVR-L2 comprising the amino acid sequence of SEQ ID NO: 16, and (iii) HVR-L3 comprising the amino acid sequence of SEQ ID NO: 17. In some embodiments, the antibody comprises: a) a VH sequence having at least 95% sequence identity to the amino acid sequence of SEQ ID NO: 8; or b) a VL sequence having at least 95% sequence identity to the amino acid sequence of SEQ ID NO: 7; or c) a VH sequence as in (a) and a VL sequence as in (b). In some embodiments, the antibody comprises a VH sequence having the amino acid sequence of SEQ ID NO: 8 or SEQ ID NO: 9. In some embodiments, the antibody comprises a VL sequence having the amino acid sequence of SEQ ID NO: 7. In some embodiments, the antibody is an IgG1, IgG2a or IgG2b antibody.

In some embodiments, an immunoconjugate comprising an antibody that binds ETBR covalently attached to a cytotoxic agent is provided, wherein the antibody comprises (a) a VH sequence having the amino acid sequence of SEQ ID NO: 8 and a VL sequence having the amino acid sequence of SEQ ID NO: 7, and wherein the cytotoxic agent is a pyrrolobenzodiazepine.

In some embodiments, the immunoconjugate has the formula Ab-(L-D)p, wherein: (a) Ab is the antibody; (b) L is a linker; (c) D is the cytotoxic agent; and (d) p ranges from 1-8.

In some such embodiments, D is a pyrrolobenzodiazepine of Formula A:

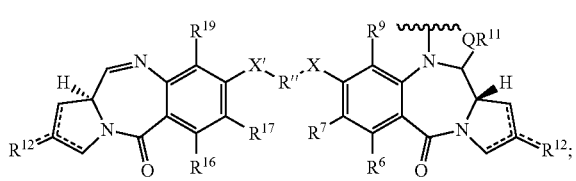

wherein the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{3-8}$ heterocyclyl and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms and/or aromatic rings that are optionally substituted; and X and X' are independently selected from O, S and N(H).

In some embodiments, D has the structure:

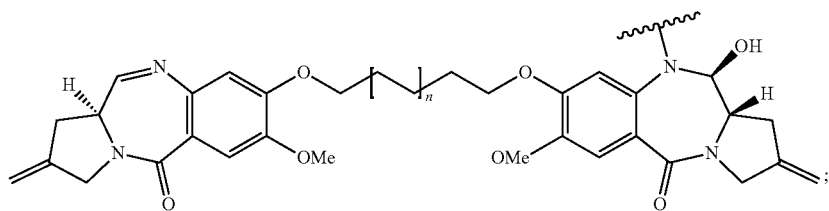

wherein n is 0 or 1.

In some embodiments, D has a structure selected from:

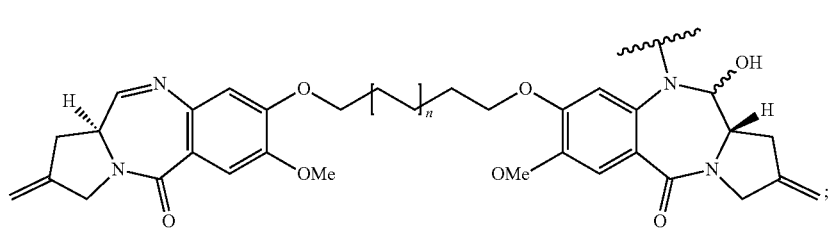

A(I)

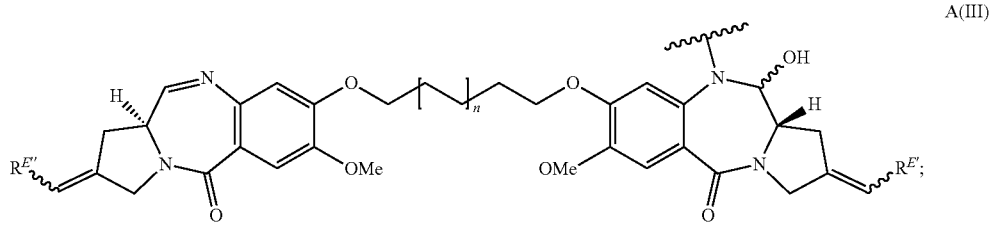

A(III)

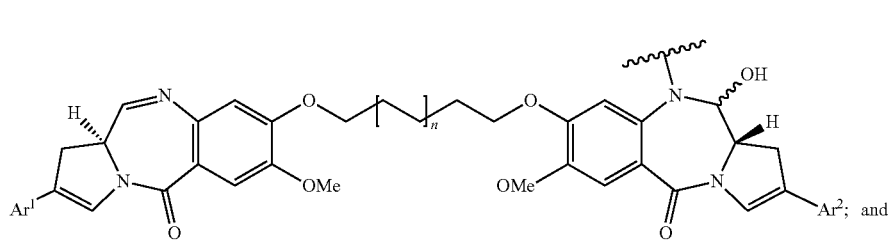

A(IV)

and

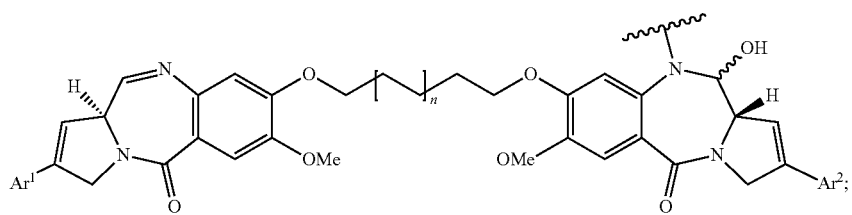

A(V)

wherein $R^E$ and $R^{E''}$ are each independently selected from H or $R^D$, wherein $R^D$ is independently selected from R, $CO_2R$, COR, CHO, $CO_2H$, and halo;

wherein $Ar^1$ and $Ar^2$ are each independently optionally substituted $C_{5-20}$ aryl; and wherein n is 0 or 1.

In some embodiments, D is a pyrrolobenzodiazepine of Formula B:

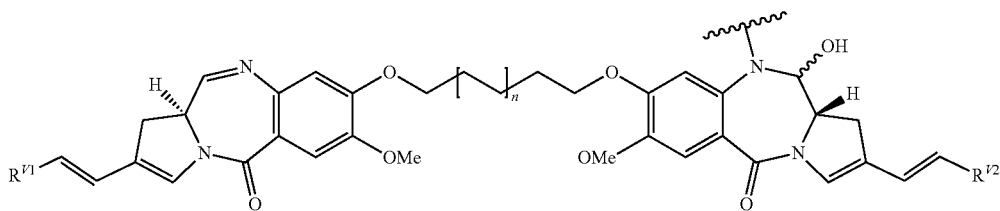

wherein the horizontal wavy line indicates the covalent attachment site to the linker;

$R^{V1}$ and $R^{V2}$ are independently selected from H, methyl, ethyl, phenyl, fluoro-substituted phenyl, and $C_{5-6}$ heterocyclyl; and n is 0 or 1.

In some embodiments, the immunoconjugate comprises a linker that is cleavable by a protease. In some such embodiments, the linker comprises a val-cit dipeptide or a Phe-homoLys dipeptide. In some embodiments, the immunoconjuge has the formula:

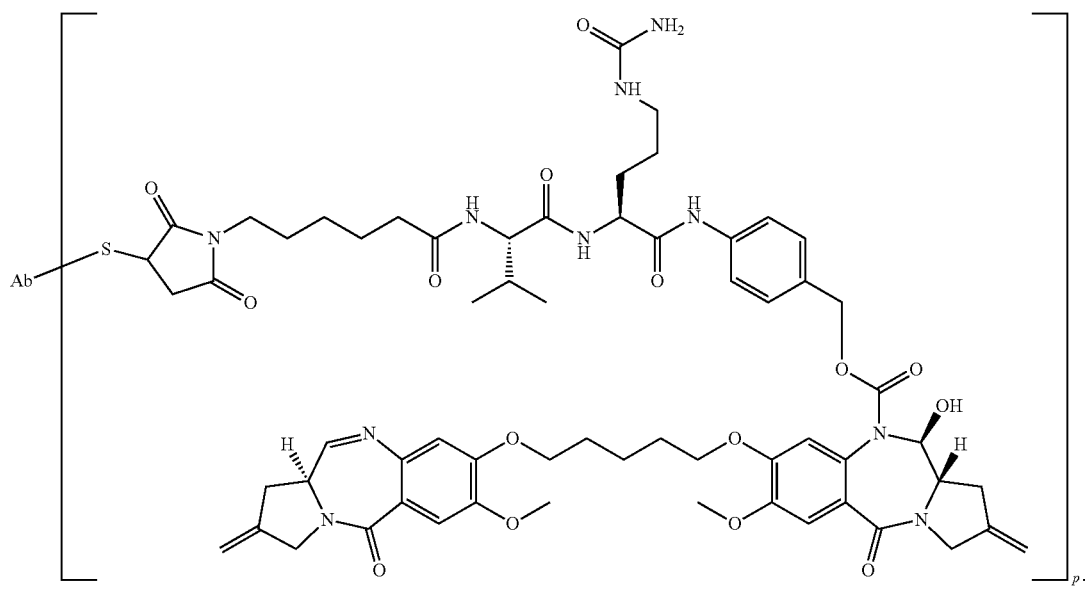

In some embodiments, p ranges from 1-3.

In some embodiments, an immunoconjugate is provided, wherein the immunoconjugate has the formula:

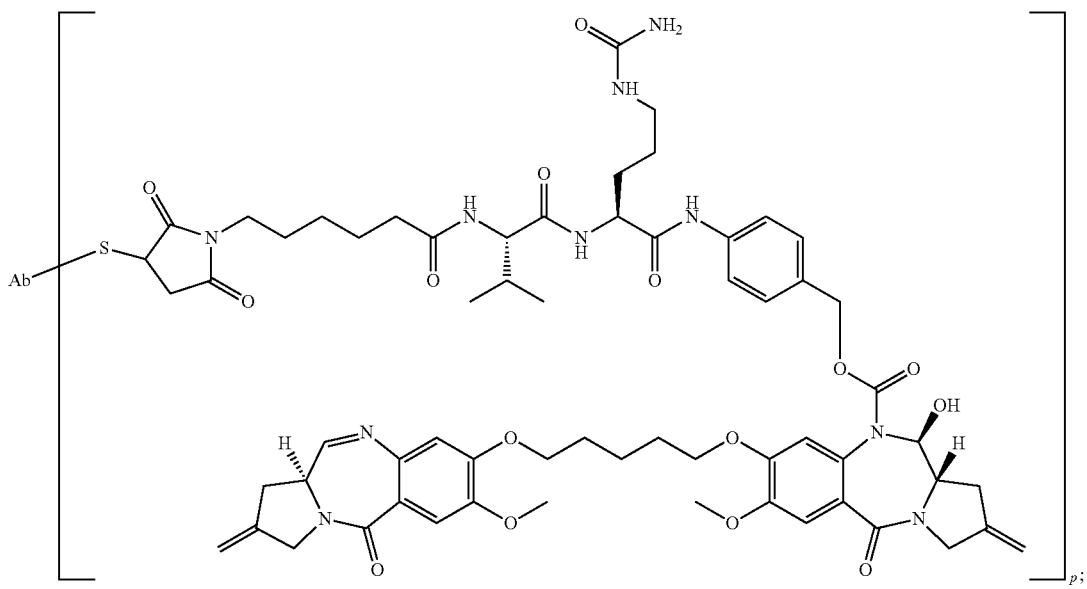

wherein Ab is an antibody comprising (i) HVR-H1 comprising the amino acid sequence of SEQ ID NO: 12, (ii) HVR-H2 comprising the amino acid sequence of SEQ ID NO: 13, (iii) HVR-H3 comprising the amino acid sequence of SEQ ID NO: 14, (iv) HVR-L1 comprising the amino acid sequence of SEQ ID NO: 15, (v) HVR-L2 comprising the amino acid sequence of SEQ ID NO: 16, and (vi) HVR-L3 comprising the amino acid sequence of SEQ ID NO: 17; and wherein p ranges from 1 to 8, or 1 to 7, or 1 to 6, or 1 to 5, or 1 to 4, or 1 to 3. In some such embodiments, the antibody comprises a VH sequence of SEQ ID NO: 8 and a VL sequence of SEQ ID NO: 7. In some embodiments, the antibody comprises a heavy chain of SEQ ID NO: 6 and a light chain of SEQ ID NO: 5.

In any of the embodiments discussed herein, the antibody may be a monoclonal antibody. In some embodiments, the antibody may be a human, humanized, or chimeric antibody. In some embodiments, the antibody is an antibody fragment that binds ETBR. In some embodiments, the antibody binds human ETBR. In some such embodiments, human ETBR has the sequence of SEQ ID NO: 10 or SEQ ID NO: 11.

In some embodiments, pharmaceutical formulations are provided, wherein the formulation comprises an immunoconjugate described herein and a pharmaceutically acceptable carrier. In some embodiments, the pharmaceutical formulation comprises an additional therapeutic agent.

In some embodiments, methods of treating an individual with an ETBR-positive cancer are provided. In some embodiments, a method comprises administering to the individual an effective amount of an immunoconjugate described herein. In some embodiments, the ETBR-positive cancer is selected from melanoma and multiple myeloma. In some embodiments, the method further comprises administering an additional therapeutic agent to the individual. In some such embodiments, the additional therapeutic agent comprises an antibody that binds melanocyte protein PMEL17. In some embodiments, the additional therapeutic agent is an immunoconjugate comprising an antibody that binds PMEL17 covalently attached to a cytotoxic agent.

In some embodiments, a method of treating an individual having an ETBR-positive cancer, wherein the ETBR-positive cancer is resistant to a first therapeutic is provided. In some embodiments, the method comprises administering to the individual an effective amount of an immunoconjugate described herein. In some embodiments, the ETBR-positive cancer is melanoma. In some embodiments, the first therapeutic comprises a first antibody that binds an antigen other than ETBR. In some embodiments, the first therapeutic is a first immunoconjugate comprising a first antibody that binds an antigen other than ETBR and a first cytotoxic agent. In some embodiments, the first antibody binds an antigen selected from PMEL17, tyrosinase-related protein 1 (TYRP1), cytotoxic T lymphocyte antigen 4 (CTLA-4), and glycoprotein NMB (GPNMB). In some embodiments, the first therapeutic comprises a first antibody that binds ETBR. In some embodiments, the first therapeutic is a first immunoconjugate comprising a first antibody that binds ETBR and a first cytotoxic agent. In some embodiments, the first cytotoxic agent and the cytotoxic agent of the immunoconjugate described herein are different. In some embodiments, the first cytotoxic agent is MMAE.

In some embodiments, a method of treating an individual with ETBR-positive cancer is provided, wherein the method comprises administering to the individual an effective amount of a first immunoconjugate described herein in combination with a second immunoconjugate comprising an antibody that binds PMEL17. In some embodiments, the antibody that binds PMEL17 comprises an HVR H1 comprising a sequence of SEQ ID NO: 21, an HVR H2 comprising a sequence of SEQ ID NO: 22, an HVR H3 comprising a sequence of SEQ ID NO: 23, an HVR L1 comprising a sequence of SEQ ID NO: 24, an HVR L2 comprising a sequence of SEQ ID NO: 25, and an HVR L3 comprising a sequence of SEQ ID NO: 26. In some embodiments, the second immunoconjugate comprises a cytotoxic agent selected from an auristatin, a pyrrolobenzodiazepine, and a nemorubicin derivative. In some embodiments, the second immunoconjugate comprises an auristatin or a nemorubicin derivative. In some embodiments, the second immunoconjugate comprises MMAE. In some such embodiments, the second immunoconjugate comprises a linker-drug portion comprising MC-val-cit-PAB-MMAE. In some embodiments, the second immunoconjugate comprises PNU-159682. In some such embodiments, the second immunoconjugate comprises MC-val-cit-PAB-PNU-159682. In any of the foregoing embodiments, the ETBR-positive cancer may be melanoma. In some embodiments, the ETBR-positive cancer is also PMEL17-positive.

In some embodiments, a method of inhibiting proliferation of an ETBR-positive cell is provided. In some such embodiments, the method comprises exposing the cell to the immunoconjugate described herein under conditions permissive for binding of the immunoconjugate to ETBR on the surface of the cell, thereby inhibiting proliferation of the cell. In some embodiments, the cell is a melanoma cell.

BRIEF DESCRIPTION OF THE FIGURES

FIG. 1 shows the amino acid sequences of the full-length light chain of the murine 5E9 monoclonal antibody (SEQ ID NO: 1) and the variable light chain of the murine 5E9 monoclonal antibody (SEQ ID NO: 3).

FIG. 2 shows the amino acid sequences of the full-length heavy chain of the murine 5E9 monoclonal antibody (SEQ ID NO: 2) and the variable heavy chain of the murine 5E9 monoclonal antibody (SEQ ID NO: 4).

FIG. 3 shows the amino acid sequences of the full-length light chain of the humanized hu5E9.v1 antibody (SEQ ID NO: 5) and the variable light chain of the humanized hu5E9.v1 antibody (SEQ ID NO: 7).

FIG. 4 shows the amino acid sequences of the full-length heavy chain of the humanized hu5E9.v1 antibody (SEQ ID NO: 6) and the variable heavy chain of the humanized hu5E9.v1 antibody (SEQ ID NO: 8).

FIG. 5 shows the amino acid sequence of the variable heavy chain of the humanized hu5E9.v2 antibody (SEQ ID NO: 9).

FIG. 6 shows the amino acid sequence of an exemplary human ETBR protein (SEQ ID NO:10) and various characteristics of the protein.

FIG. 9 shows expression of ETBR (also referred to as "EDNRB") in parental and resistant UACC-257X2.2 cells derived in vivo (A) and in vitro (B), as described in Example B.

DETAILED DESCRIPTION

I. Definitions

Figure 7:
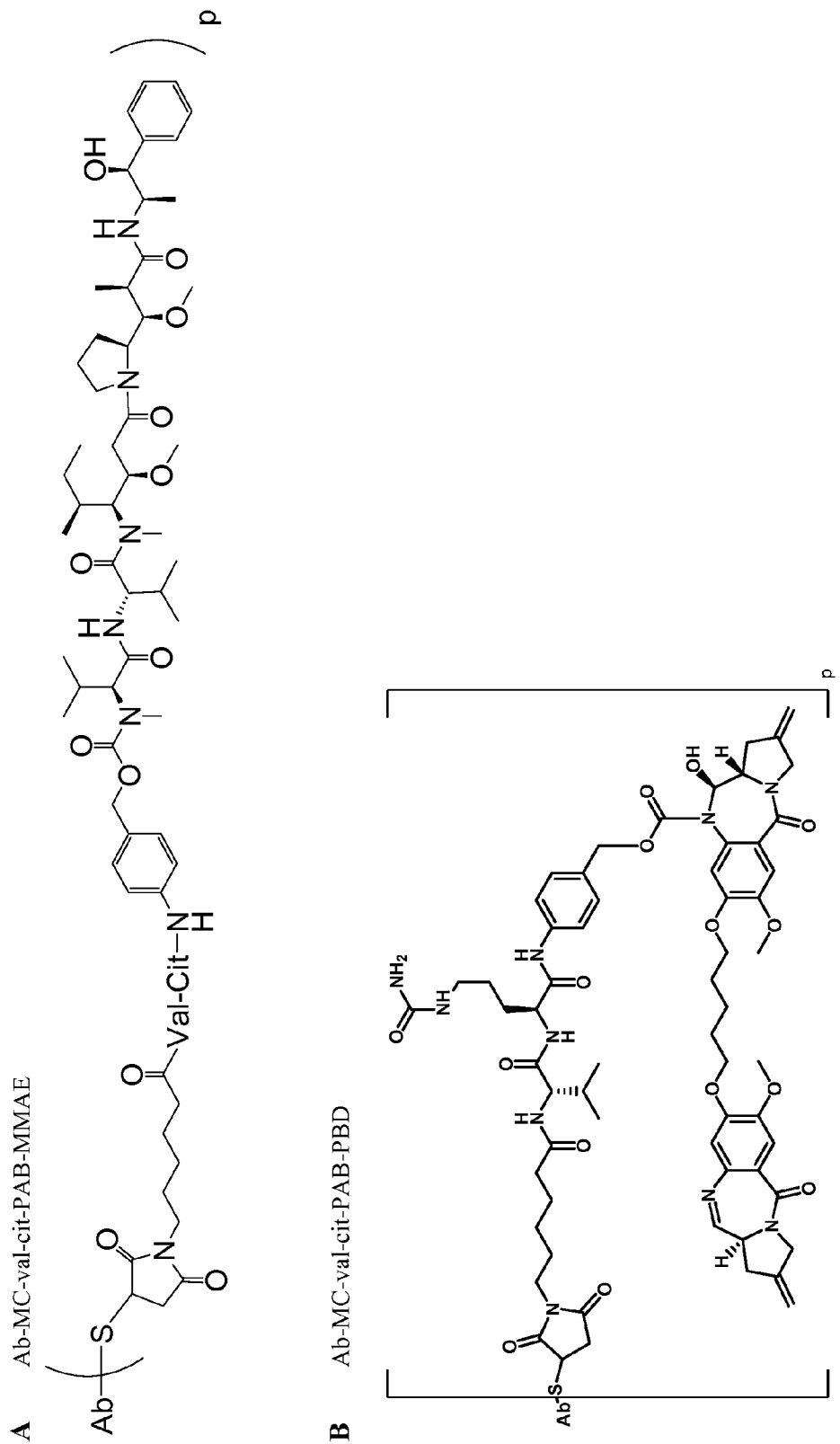
FIG. 7 shows the structures of various antibody-drug conjugates, including (A) Ab-MC-val-cit-PAB-MMAE and (B) Ab-MC-val-cit-PAB-PBD.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-ETBR antibody" and "an antibody that binds to ETBR" refer to an antibody that is capable of binding ETBR with sufficient affinity such that the antibody is useful as a diagnostic and/or therapeutic agent in targeting ETBR. In one embodiment, the extent of binding of an anti-ETBR antibody to an unrelated, non-ETBR protein is less than about 10% of the binding of the antibody to ETBR as measured, e.g., by a radioimmunoassay (RIA). In certain embodiments, an antibody that binds to ETBR has a dissociation constant (Kd) of ≤1 µM, ≤100 nM, ≤10 nM, ≤5 Nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-ETBR antibody binds to an epitope of ETBR that is conserved among ETBR from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, melanoma, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gammaI1 and calicheamicin omegaI1 (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®; Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and docetaxel (TAXOTERE®; Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone; CVP, an abbreviation for a combined therapy of cyclophosphamide, vincristine, and prednisolone; and FOLFOX, an abbreviation for a treatment regimen with oxaliplatin (ELOXATIN™) combined with 5-FU and leucovorin.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) or complementarity determining region (CDR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of ETBR" refers to naturally occurring forms of ETBR that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-ETBR antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "ETBR," as used herein, refers to any native ETBR from any vertebrate source, including mammals such as primates (e.g. humans, cynomolgus monkey (cyno)) and rodents (e.g., mice and rats), unless otherwise indicated. The term encompasses "full-length," unprocessed ETBR as well as any form of ETBR that results from processing in the cell. The term also encompasses naturally occurring variants of ETBR, e.g., splice variants, allelic variants, and isoforms. The amino acid sequence of an exemplary human ETBR precursor (with signal sequence) is shown in SEQ ID NO: 10. The amino acid sequence of an exemplary human mature ETBR (without signal sequence) is shown in SEQ ID NO: 11.

The term "ETBR-positive cancer" refers to a cancer comprising cells that express ETBR on their surface.

The term "ETBR-positive cell" refers to a cell that expresses ETBR on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, immunoconjugates of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The phrase "optionally substituted" as used herein, pertains to a parent group that may be unsubstituted or that may be substituted.

Unless otherwise specified, the term "substituted" as used herein, pertains to a parent group that bears one or more substituents. The term "substituent" is used herein in the conventional sense and refers to a chemical moiety that is covalently attached to, or if appropriate, fused to, a parent group. A wide variety of substituents are known, and methods for their formation and introduction into a variety of parent groups are also known.

In some embodiments, the substituents described herein (which include optional substituents) are limited to those groups that are not reactive to the antibody. In some embodiments, the link to the antibody is formed from the N10 position of the PBD compound through the linker (L). In some instances, reactive functional groups located at other parts of the PBD structure may be capable of forming additional bonds to the antibody (this may be referred to as crosslinking). Such additional bonds, in some instances, may alter transport and biological activity of the conjugate. Therefore, in some embodiments, the additional substituents are limited to those lacking reactive functionality.

In some embodiments, the substituents are selected from R, OR, SR, NRR', $NO_2$, halo, $CO_2R$, COR, $CONH_2$, CONHR, and CONRR'. In some embodiments, the substituents are selected from R, OR, SR, NRR', $NO_2$, $CO_2R$, COR, $CONH_2$, CONHR, and CONRR'. In some embodiments, the substituents are selected from R, OR, SR, NRR', $NO_2$, and halo. In some embodiments, the substituents are selected from the group consisting of R, OR, SR, NRR', and $NO_2$.

Any of the embodiments discussed above may be applied to any of the substituents described herein. Alternatively, the substituents may be selected from one or more of the groups discussed below.

The term "$C_{1-12}$ alkyl" as used herein, pertains to a monovalent moiety obtained by removing a hydrogen atom from a carbon atom of a hydrocarbon compound having from 1 to 12 carbon atoms, which is aliphatic, and which may be cyclic or acyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl (C1), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include, but are not limited to, iso-propyl ($C_3$), iso-butyl ($C_4$), sec-butyl ($C_4$), tert-butyl ($C_4$), iso-pentyl ($C_5$), and neo-pentyl ($C_5$).

An alkyl group may optionally be interrupted by one or more heteroatoms selected from O, N(H) and S. Such groups may be referred to as "heteroalkyl".

The term "$C_{2-12}$ heteroalkyl" as used herein, pertains to a monovalent moiety obtained by removing a hydrogen atom from a carbon atom of a hydrocarbon compound having from 2 to 12 carbon atoms, and one or more heteroatoms selected from O, N(H) and S, preferably O and S.

Examples of heteroalkyl groups include, but are not limited to, those comprising one or more ethylene glycol units of the type —(OCH$_2$CH$_2$)—. The terminus of a heteroalkyl group may be the primary form of a heteroatom, e.g. —OH, —SH or —NH$_2$. In a preferred embodiment, the terminus is —CH$_3$.

The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

(i) saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

(ii) unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and (iii) saturated polycyclic hydrocarbon compounds:
norcarane ($C_7$), norpinane ($C_7$), norbornane ($C_7$).

The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. In some embodiments, each ring has from 3 to 7 ring atoms, of which from 1 to 4 are ring heteroatoms.

As used herein, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:
(i) $N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
(ii) $O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
(iii) $S_1$: thiirane ($C_3$), thietane ($C_4$), thiolane (tetrahydrothiophene) ($C_5$), thiane (tetrahydrothiopyran) ($C_6$), thiepane ($C_7$);
(iv) $O_2$: dioxolane ($C_5$), dioxane ($C_6$), and dioxepane ($C_7$);
(v) $O_3$: trioxane ($C_6$);
(vi) $N_2$: imidazolidine ($C_5$), pyrazolidine (diazolidine) ($C_5$), imidazoline ($C_5$), pyrazoline (dihydropyrazole) ($C_5$), piperazine ($C_6$);
(vii) $N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
(viii) $N_1S_1$: thiazoline ($C_5$), thiazolidine ($C_5$), thiomorpholine ($C_6$);
(ix) $N_2O_1$: oxadiazine ($C_6$);
(x) $O_1S_1$: oxathiole ($C_5$) and oxathiane (thioxane) ($C_6$); and,
(xi) $N_1O_1S_1$: oxathiazine ($C_6$).

Examples of substituted monocyclic heterocyclyl groups include, but are not limited to, those derived from saccharides, in cyclic form, for example, furanoses ($C_5$), such as arabinofuranose, lyxofuranose, ribofuranose, and xylofuranase, and pyranoses ($C_6$), such as allopyranose, altropyranose, glucopyranose, mannopyranose, gulopyranose, idopyranose, galactopyranose, and talopyranose.

The term "$C_{5-20}$ aryl", as used herein, pertains to a monovalent moiety obtained by removing a hydrogen atom from an aromatic ring atom of an aromatic compound, which moiety has from 3 to 20 ring atoms. In some embodiments, each ring has from 5 to 7 ring atoms.

In some embodiments, the ring atoms are all carbon atoms, as in "carboaryl groups". Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

In some embodiments, the ring atoms may include one or more heteroatoms, as in "heteroaryl groups". Examples of monocyclic heteroaryl groups include, but are not limited to, those derived from:
(i) $N_1$: pyrrole (azole) ($C_5$), pyridine (azine) ($C_6$);
(ii) $O_1$: furan (oxole) ($C_5$);
(iii) $S_1$: thiophene (thiole) ($C_5$);
(iv) $N_1O_1$: oxazole ($C_5$), isoxazole ($C_5$), isoxazine ($C_6$);
(v) $N_2O_1$: oxadiazole (furazan) ($C_5$);
(vi) $N_3O_1$: oxatriazole ($C_5$);
(vii) $N_1S_1$: thiazole ($C_5$), isothiazole ($C_5$);
(viii) $N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
(ix) $N_3$: triazole ($C_5$), triazine ($C_6$); and,
(x) $N_4$: tetrazole ($C_5$).

Examples of heteroaryl which comprise fused rings, include, but are not limited to:
(i) $C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$); benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
(ii) $C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);
(iii) $C_{11}$ (with 2 fused rings) derived from benzodiazepine ($N_2$);
(iv) $C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
(v) $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group). In some embodiments, R is a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group. In some embodiments, R$^1$ and/or R$^2$ are independently a $C_{1-7}$ alkyl group. In some embodiments, in the case of a "cyclic" acetal group, R$^1$ and R$^2$, taken together with the two oxygen atoms to which they are attached, and the carbon atom to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group. In some embodiments, R$^1$ is a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group. In some embodiments, R is a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group. In some embodiments, R is a $C_{1-7}$ alkyl group. Examples of hemiketal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group. In some embodiments, R is hydrogen or a $C_{1-7}$ alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl). In some embodiments, R is a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarbonyloxy: —OC(=O)OR, wherein R is an ester substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of oxycarbonyloxy groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group. In some embodiments, R$^1$ and R$^2$ are independently H or a $C_{1-7}$ alkyl group. In some embodiments, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of thioamido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, and R$^2$ is an acyl substituent, for example, a $C_{1-7}$ alkyl group, a $C_{3-20}$ heterocyclyl group, or a $C_{5-20}$ aryl group. In some embodiments, R$^1$ and/or R$^2$ is hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

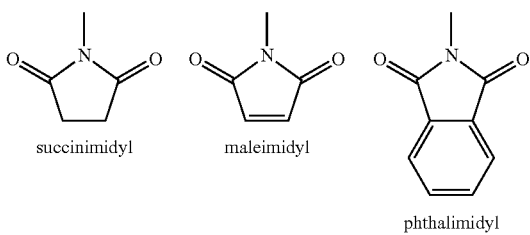

succinimidyl  maleimidyl  phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-2}$ alkyl group, a $C_{3-20}$ heterocyclyl group, or a $C_{5-20}$ aryl group. In some embodiments, R$^1$ is hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

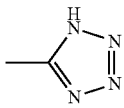

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group. In some embodiments, each R is H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group. In some embodiments, R is a $C_{1-7}$ alkyl group. Examples of thioether groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group. In some embodiments, R is a $C_{1-7}$ alkyl group (also referred to herein as $C_{1-7}$ alkyl disulfide). Examples of disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group. In some embodiments, R is a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfuric acid ester): —S(=O)OR; wherein R is a sulfinate substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR¹S(=O)₂OH, wherein R¹ is an amino substituent, as defined for amino groups. Examples of sulfamino groups include, but are not limited to, —NHS(=O)₂OH and —N(CH₃)S(=O)₂OH.

Sulfonamino: —NR¹S(=O)₂R, wherein R¹ is an amino substituent, as defined for amino groups, and R is a sulfonamino substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$ alkyl group, a $C_{3-20}$ heterocyclyl group, or a $C_{5-20}$ aryl group. In some embodiments, R is a $C_{1-7}$ alkyl group. Examples of sulfinamino groups include, but are not limited to, —NHS(=O)CH₃ and —N(CH₃)S(=O)C₆H₅.

Phosphino (phosphine): —PR₂, wherein R is a phosphino substituent, for example, —H, a $C_{1-7}$ alkyl group, a $C_{3-20}$ heterocyclyl group, or a $C_{5-20}$ aryl group. In some embodiments, R is —H, a $C_{1-7}$ alkyl group, or a $C_{5-20}$ aryl group. Examples of phosphino groups include, but are not limited to, —PH₂, —P(CH₃)₂, —P(CH₂CH₃)₂, —P(t-Bu)₂, and —P(Ph)₂.

Phospho: —P(=O)₂.

Phosphinyl (phosphine oxide): —P(=O)R₂, wherein R is a phosphinyl substituent, for example, a $C_{1-7}$ alkyl group, a $C_{3-20}$ heterocyclyl group, or a $C_{5-20}$ aryl group. In some embodiments, R is a $C_{1-7}$ alkyl group or a $C_{5-20}$ aryl group. Examples of phosphinyl groups include, but are not limited to, —P(=O)(CH₃)₂, —P(=O)(CH₂CH₃)₂, —P(=O)(t-Bu)₂, and —P(=O)(Ph)₂.

Phosphonic acid (phosphono): —P(=O)(OH)₂.

Phosphonate (phosphono ester): —P(=O)(OR)₂, where R is a phosphonate substituent, for example, —H, a $C_{1-7}$ alkyl group, a $C_{3-20}$ heterocyclyl group, or a $C_{5-20}$ aryl group. In some embodiments, R is —H, a $C_{1-7}$ alkyl group, or a $C_{5-20}$ aryl group. Examples of phosphonate groups include, but are not limited to, —P(=O)(OCH₃)₂, —P(=O)(OCH₂CH₃)₂, —P(=O)(O-t-Bu)₂, and —P(=O)(OPh)₂.

Phosphoric acid (phosphonooxy): —OP(=O)(OH)₂.

Phosphate (phosphonooxy ester): —OP(=O)(OR)₂, where R is a phosphate substituent, for example, —H, a $C_{1-7}$ alkyl group, a $C_{3-20}$ heterocyclyl group, or a $C_{5-20}$ aryl group. In some embodiments, R is —H, a $C_{1-7}$ alkyl group, or a $C_{5-20}$ aryl group. Examples of phosphate groups include, but are not limited to, —OP(=O)(OCH₃)₂, —OP(=O)(OCH₂CH₃)₂, —OP(=O)(O-t-Bu)₂, and —OP(=O)(OPh)₂.

Phosphorous acid: —OP(OH)₂

Phosphite: —OP(OR)₂, where R is a phosphite substituent, for example, —H, a $C_{1-7}$ alkyl group, a $C_{3-20}$ heterocyclyl group, or a $C_{5-20}$ aryl group. In some embodiments, R is —H, a $C_{1-7}$ alkyl group, or a $C_{5-20}$ aryl group. Examples of phosphite groups include, but are not limited to, —OP(OCH₃)₂, —OP(OCH₂CH₃)₂, —OP(O-t-Bu)₂, and —OP(OPh)₂.

Phosphoramidite: —OP(OR¹)—NR²₂, where R¹ and R² are phosphoramidite substituents, for example, —H, a (optionally substituted) $C_{1-7}$ alkyl group, a $C_{3-20}$ heterocyclyl group, or a $C_{5-20}$ aryl group. In some embodiments, R is —H, a $C_{1-7}$ alkyl group, or a $C_{5-20}$ aryl group. Examples of phosphoramidite groups include, but are not limited to, —OP(OCH₂CH₃)—N(CH₃)₂, —OP(OCH₂CH₃)—N(i-Pr)₂, and —OP(OCH₂CH₂CN)—N(i-Pr)₂.

Phosphoramidate: —OP(=O)(OR¹)—NR²₂, where R¹ and R² are phosphoramidate substituents, for example, —H, a (optionally substituted) $C_{1-7}$ alkyl group, a $C_{3-20}$ heterocyclyl group, or a $C_{5-20}$ aryl group. In some embodiments, R¹ and R² are —H, a $C_{1-7}$ alkyl group, or a $C_{5-20}$ aryl group. Examples of phosphoramidate groups include, but are not limited to, —OP(=O)(OCH₂CH₃)—N(CH₃)₂, —OP(=O)(OCH₂CH₃)—N(i-Pr)₂, and —OP(=O)(OCH₂CH₂CN)—N(i-Pr)₂.

The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which is aliphatic, and which may be cyclic or acyclic, and which may be saturated, partially unsaturated, or fully unsaturated. Thus, the term "alkylene" includes the sub-classes alkenylene, alkynylene, cycloalkylene, etc., discussed below.

Examples of linear saturated $C_{3-12}$ alkylene groups include, but are not limited to, —(CH₂)ₙ— where n is an integer from 3 to 12, for example, —CH₂CH₂CH₂— (propylene), —CH₂CH₂CH₂CH₂— (butylene), —CH₂CH₂CH₂CH₂CH₂— (pentylene) and —CH₂CH₂CH₂CH₂CH₂CH₂CH₂— (heptylene).

Examples of branched saturated $C_{3-12}$ alkylene groups include, but are not limited to, —CH(CH₃)CH₂—, —CH(CH₃)CH₂CH₂—, —CH(CH₃)CH₂CH₂CH₂—, —CH₂CH(CH₃)CH₂—, —CH₂CH(CH₃)CH₂CH₂—, —CH(CH₂CH₃)—, —CH(CH₂CH₃)CH₂—, and —CH₂CH(CH₂CH₃)CH₂—.

Examples of linear partially unsaturated $C_{3-12}$ alkylene groups ($C_{3-12}$ alkenylene, and alkynylene groups) include, but are not limited to, —CH=CH—CH₂—, —CH₂—CH=CH₂—, —CH=CH—CH₂—CH₂—, —CH=CH—CH₂—CH₂—CH₂—, —CH=CH—CH=CH—, —CH=CH—CH=CH—CH₂—, —CH=CH—CH₂—CH=CH—, —CH=CH—CH₂—CH₂—CH=CH—, and —CH₂—C≡C—CH₂—.

Examples of branched partially unsaturated $C_{3-12}$ alkylene groups ($C_{3-12}$ alkenylene and alkynylene groups) include, but are not limited to, —C(CH₃)=CH—, —C(CH₃)=CH—CH₂—, —CH=CH—CH(CH₃)— and —C≡C—CH(CH₃)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

"Linker" refers to a chemical moiety comprising a covalent bond or a chain of atoms that covalently attaches an antibody to a drug moiety. Nonlimiting exemplary linkers are described herein.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to ETBR and immunoconjugates comprising such antibodies. Antibodies and immunoconjugates of the invention are useful, e.g., for the diagnosis or treatment of ETBR-positive cancers.

A. Exemplary Anti-ETBR Antibodies

In some embodiments, isolated antibodies that bind to ETBR are provided. ETBR is a G-protein coupled receptor expressed in melanocytes.

An exemplary naturally occurring human ETBR precursor sequence, with signal sequence (amino acids 1 to 26) is provided in SEQ ID NO: 10, and the corresponding mature ETBR sequence is shown in SEQ ID NO: 11 (corresponding to amino acids 27 to 442 of SEQ ID NO: 10).

In certain embodiments, an anti-ETBR antibody binds an epitope within amino acids 64 to 101 of SEQ ID NO: 10. Nonlimiting exemplary such antibodies include 5E9 and humanized versions thereof. In some embodiments, an anti-ETBR antibody binds human ETBR. In some embodiments, an anti-ETBR antibody binds human ETBR and cynomolgus monkey ETBR.

In some embodiments, an anti-ETBR antibody binds human ETBR with an affinity of ≤10 nM, or ≤7 nM, or ≤6 nM, or ≤5 nM, or ≤4 nM and optionally ≥0.0001 nM, or ≥0.001 nM, or ≥0.01 nM. Nonlimiting exemplary such antibodies include mu5E9, hu5E9.v1, and hu5E9.v2, which bind to human ETBR with an affinity of 5 nM and 3.7 nM, respectively.

Assays

To determine whether an anti-ETBR antibody "binds to an epitope within amino acids 64 to 101 of SEQ ID NO: 10," ETBR polypeptides with N- and C-terminal deletions are expressed in mammalian cells (such as CHO cells or 293 cells) and binding of the antibody to the truncated polypeptides is tested by FACS. A substantial reduction (≥70% reduction) or elimination of binding of the antibody to a truncated polypeptide relative to binding to full-length ETBR expressed in cells indicates that the antibody does not bind to that truncated polypeptide. Alternatively, in some embodiments, whether an anti-ETBR antibody "binds to an epitope within amino acids 64 to 101 of SEQ ID NO: 10" is determined using an ELISA assay. A substantial reduction (≥70% reduction) or elimination of binding of the antibody to a truncated polypeptide relative to binding to a longer portion of ETBR, such as the extracellular domain, indicates that the antibody does not bind to that truncated polypeptide.

Whether an anti-ETBR antibody "binds with an affinity of" ≤10 nM, or ≤7 nM, or ≤6 nM, or ≤5 nM, or ≤4 nM, is determined using mammalian cells (such as CHO cells or 293 cells) expressing ETBR on the surface in a competition assay using serially diluted, unlabeled anti-ETBR antibody. Binding affinity, $K_D$, of the antibodies may be determined in accordance with standard Scatchard analysis performed utilizing a non-linear curve fitting program (see, for example, Munson et al., Anal Biochem, 107: 220-239, 1980). In some embodiments, whether an anti-ETBR antibody "binds with an affinity of" ≤10 nM, or ≤7 nM, or ≤6 nM, or ≤5 nM, or ≤4 nM, may be determined using surface plasmon resonance, such as a Biacore™ assay, or kinetic exclusion assay (KinExA®, Sapidyne Instruments, Boise, Id.).

Antibody 5E9 and Other Embodiments

In some embodiments, the invention provides an anti-ETBR antibody or immunoconjugate comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17.

In one aspect, the invention provides an antibody or immunoconjugate comprising at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In one embodiment, the antibody comprises HVR-H3 comprising the amino acid sequence of SEQ ID NO: 14. In another embodiment, the antibody comprises HVR-H3 comprising the amino acid sequence of SEQ ID NO: 14 and HVR-L3 comprising the amino acid sequence of SEQ ID NO: 17. In a further embodiment, the antibody comprises HVR-H3 comprising the amino acid sequence of SEQ ID NO: 14, HVR-L3 comprising the amino acid sequence of SEQ ID NO: 17, and HVR-H2 comprising the amino acid sequence of SEQ ID NO: 15. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the invention provides an antibody or immunoconjugate comprising at least one, at least two, or all three VL HVR sequences selected from (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17. In another aspect, the invention provides an antibody or immunoconjugate comprising at least one, at least two, or all three VL HVR sequences selected from (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17. In one embodiment, the antibody comprises (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17. In one embodiment, the antibody comprises (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17.

In another aspect, an antibody of the invention or immunoconjugate comprises (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 15, (ii) HVR-L2 comprising the amino acid sequence of SEQ ID NO: 16, and (c) HVR-L3 comprising the amino acid sequence of SEQ ID NO: 17. In another aspect, an antibody or immunoconjugate of the invention comprises (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 15, (ii) HVR-L2 comprising the amino acid sequence of SEQ ID NO: 16, and (c) HVR-L3 comprising the amino acid sequence of SEQ ID NO: 17.

In another aspect, the invention provides an antibody or immunoconjugate comprising (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17. In another aspect, the invention provides an antibody or immunoconjugate comprising (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17.

In any of the above embodiments, an anti-ETBR antibody is humanized. In one embodiment, an anti-ETBR antibody comprises HVRs as in any of the above embodiments, and further comprises a human acceptor framework, e.g. a human immunoglobulin framework or a human consensus framework. In certain embodiments, the human acceptor framework is the human VL kappa 1 ($VL_{KI}$) framework and/or the VH framework $VH_{III}$. In some embodiments, a humanized anti-ETBR antibody comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17. In some embodiments, a humanized anti-ETBR antibody comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17.

In another aspect, an anti-ETBR antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In certain embodiments, a VH sequence having at least 90%, 91%, 92%, 93%, 94%, 95%, 96%, 97%, 98%, or 99% identity to the amino acid sequence of SEQ ID NO: 8 contains substitutions (e.g., conservative substitutions), insertions, or deletions relative to the reference sequence, but an anti-ETBR antibody comprising that sequence retains the ability to bind to ETBR. In certain embodiments, a total of 1 to 10 amino acids have been substituted, inserted and/or deleted in SEQ ID NO: 8. In certain embodiments, a total of 1 to 5 amino acids have been substituted, inserted and/or deleted in SEQ ID NO: 8. In certain embodiments, substitutions, insertions, or deletions occur in regions outside the HVRs (i.e., in the FRs).

Optionally, the anti-ETBR antibody comprises a VH sequence selected from SEQ ID NOs: 4, 8, and 9, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In some embodiments, an anti-ETBR antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99° A identity to the amino acid sequence of SEQ ID NO: 7 contains substitutions (e.g., conservative substitutions), insertions, or deletions relative to the reference sequence, but an anti-ETBR antibody comprising that sequence retains the ability to bind to ETBR. In certain embodiments, a total of 1 to 10 amino acids have been substituted, inserted and/or deleted in SEQ ID NO: 7. In certain embodiments, a total of 1 to 5 amino acids have been substituted, inserted and/or deleted in SEQ ID NO: 7. In certain embodiments, the substitutions, insertions, or deletions occur in regions outside the HVRs (i.e., in the FRs). Optionally, the anti-ETBR antibody comprises the VL sequence of SEQ ID NO: 3 or SEQ ID NO: 7, including post-translational modifications of that sequence. In a particular embodiment, the VL comprises one, two or three HVRs selected from (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17.

In another aspect, an anti-ETBR antibody is provided, wherein the antibody comprises a VH as in any of the embodiments provided above, and a VL as in any of the embodiments provided above. In some embodiments, the antibody comprises the VH and VL sequences in SEQ ID NO: 8 and SEQ ID NO: 7, respectively, including post-translational modifications of those sequences. In some embodiments, the antibody comprises the VH and VL sequences in SEQ ID NO: 9 and SEQ ID NO: 7, respectively, including post-translational modifications of those sequences. In some embodiments, the antibody comprises the heavy chain and light chain sequences in SEQ ID NO: 6 and SEQ ID NO: 5, respectively, including post-translational modifications of those sequences. In some embodiments, the antibody comprises the heavy chain and light chain sequences in SEQ ID NO: 6 and SEQ ID NO: 18, respectively, including post-translational modifications of those sequences. In some embodiments, the antibody comprises the heavy chain and light chain sequences in SEQ ID NO: 19 and SEQ ID NO: 5, respectively, including post-translational modifications of those sequences. In some embodiments, the antibody comprises the heavy chain and light chain sequences in SEQ ID NO: 20 and SEQ ID NO: 5, respectively, including post-translational modifications of those sequences.

In a further aspect, the invention provides an antibody or immunoconjugate that binds to the same epitope as an anti-ETBR antibody provided herein. For example, in certain embodiments, an antibody or immunoconjugate is provided that binds to the same epitope as an anti-ETBR antibody comprising a VH sequence of SEQ ID NO: 8 and a VL sequence of SEQ ID NO: 7. In certain embodiments, an antibody is provided that binds to an epitope of SEQ ID NO: 10 from, within, or overlapping amino acids 64 to 101.

In a further aspect of the invention, an anti-ETBR antibody according to any of the above embodiments is a monoclonal antibody, including a chimeric, humanized or human antibody. In one embodiment, an anti-ETBR antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In any of the immunoconjugates described above, the antibody may be conjugated to a drug moiety. In some embodiments, the antibody is conjugated to a cytotoxic agent. In some such embodiments, the cytotoxic agent is a pyrrolobenzodiazepine (PBD), such as a PBD dimer Various nonlimiting exemplary PBD dimers are discussed herein.

In a further aspect, an anti-ETBR antibody or immunoconjugate according to any of the above embodiments may incorporate any of the features, singly or in combination, as described in Sections 1-7 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM, and optionally is ≥$10^{-13}$ M. (e.g. $10^{-8}$M or less, e.g. from $10^{-8}$M to $10^{-13}$M, e.g., from $10^{-9}$M to $10^{13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (f0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ See, e.g., Chen et al., *J. Mol.*

Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., Nature 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006).

Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for ETBR and the other is for any other antigen. In certain embodiments, bispecific antibodies may bind to two different epitopes of ETBR. Bispecific antibodies may also be used to localize cytotoxic agents to cells which express ETBR. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J*. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to ETBR as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity.

Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Nonlimiting exemplary cysteine engineered heavy chains and light chains of anti-ETBR antibodies are shown in SEQ ID NOs: 18, 19, and 20. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-ETBR antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-ETBR antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-ETBR antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977));

baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, N.J.), pp. 255-268 (2003).

C. Assays

Anti-ETBR antibodies provided herein may be identified, screened for, or characterized for their physical/chemical properties and/or biological activities by various assays known in the art.

In one aspect, an antibody is tested for its antigen binding activity, e.g., by known methods such as ELISA, BIA-Core®, FACS, or Western blot.

In another aspect, competition assays may be used to identify an antibody that competes with any of the antibodies described herein for binding to ETBR. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized ETBR is incubated in a solution comprising a first labeled antibody that binds to ETBR (e.g., any of the antibodies described herein) and a second unlabeled antibody that is being tested for its ability to compete with the first antibody for binding to ETBR. The second antibody may be present in a hybridoma supernatant. As a control, immobilized ETBR is incubated in a solution comprising the first labeled antibody but not the second unlabeled antibody. After incubation under conditions permissive for binding of the first antibody to ETBR, excess unbound antibody is removed, and the amount of label associated with immobilized ETBR is measured. If the amount of label associated with immobilized ETBR is substantially reduced in the test sample relative to the control sample, then that indicates that the second antibody is competing with the first antibody for binding to ETBR. See Harlow and Lane (1988) Antibodies: A Laboratory Manual ch. 14 (Cold Spring Harbor Laboratory, Cold Spring Harbor, N.Y.).

D. Immunoconjugates

The invention also provides immunoconjugates comprising an anti-ETBR antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Exemplary drug moieties include, but are not limited to, pyrrolobenzodiazepine (PBD) and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

Ab-(L-D)$_p$     I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

-A$_a$-W$_w$-Y$_y$-  II wherein A is a "stretcher unit", and a is an integer from 0 to 1; W is an "amino acid unit", and w is an integer from 0 to 12; Y is a "spacer unit", and y is 0, 1, or 2. An ADC comprising the linker of Formula II has the Formula I(A): Ab-(A$_a$-W$_w$-Y$_y$-D)p, wherein Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

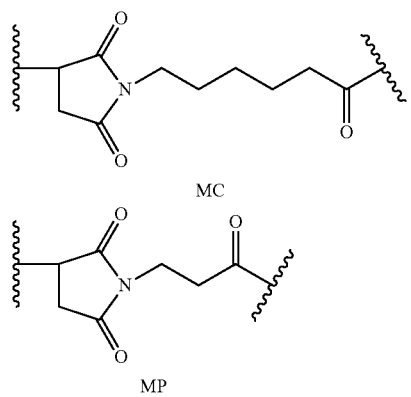

MC

MP

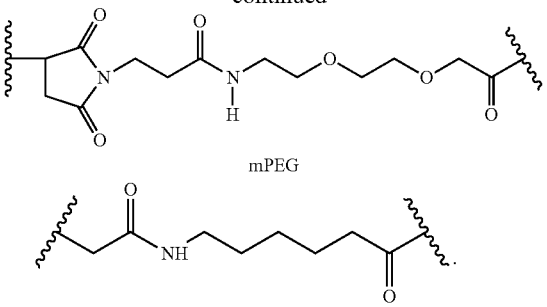

mPEG

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schröder and K. Lübke (1965) "The Peptides", volume 1, pp 76-136, Academic Press).

In some embodiments, a linker component comprises a "spacer unit" (Y) that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). In some embodiments, the spacer unit comprises p-aminobenzyloxycarbonyl (PAB). In some embodiments, an ADC comprising a self-immolative linker has the structure:

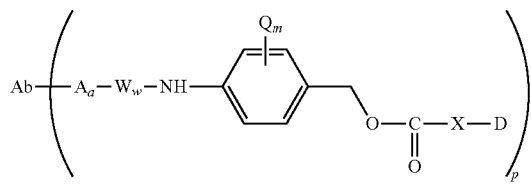

wherein Q is —$C_1$-$C_8$ alkyl, —O—($C_1$-$C_8$ alkyl), -halogen, -nitro, or -cyano; m is an integer ranging from 0 to 4; X may be one or more additional spacer units or may be absent; and p ranges from 1 to about 20. In some embodiments, p ranges from 1 to 10, 1 to 7, 1 to 5, or 1 to 4. Nonlimiting exemplary X spacer units include:

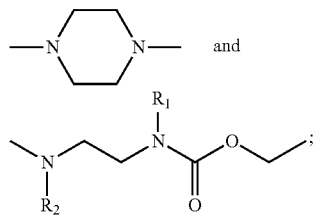

wherein $R_1$ and $R_2$ are independently selected from H and $C_1$-$C_6$ alkyl. In some embodiments, R1 and R2 are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J. Amer. Chem. Soc.* 94:5815) and 2-aminophenylpropionic acid amides (Amsberry, et al (1990) *J. Org. Chem.* 55:5867). Linkage of a drug to the α-carbon of a glycine residue is another example of a self-immolative spacer that may be useful in ADC (Kingsbury et al (1984) *J. Med. Chem.* 27:1447).

In some embodiments, linker L may be a dendritic type linker for covalent attachment of more than one drug moiety to an antibody through a branching, multifunctional linker moiety (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

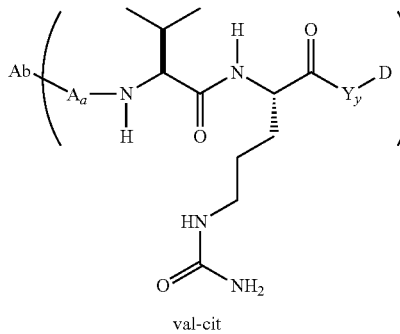
val-cit

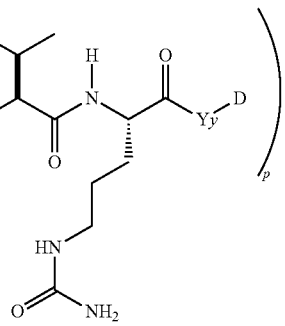
MC-val-cit

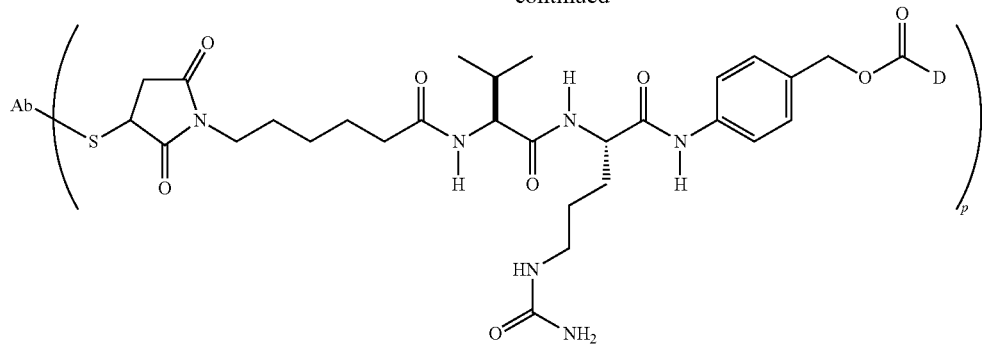
MC-val-cit-PAB
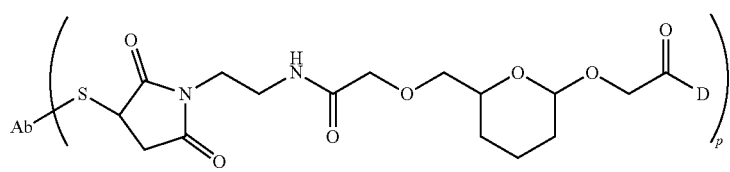
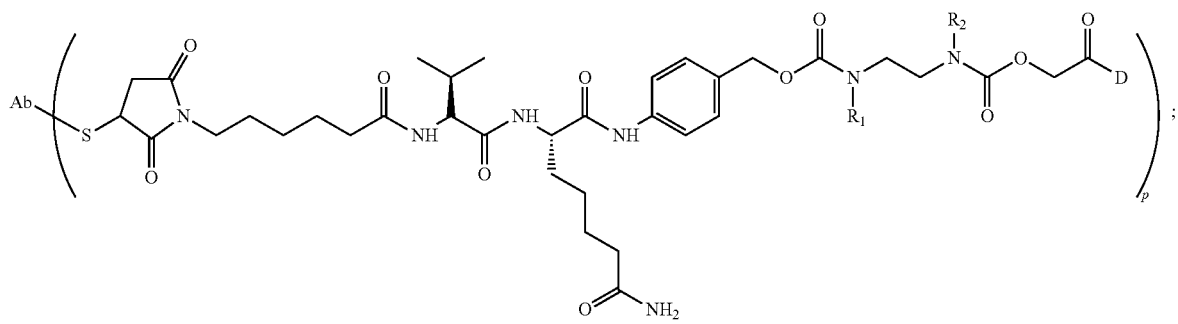
wherein $R_1$ and $R_2$ are independently selected from H and $C_1$-$C_6$ alkyl. In some embodiments, R1 and R2 are each —$CH_3$.
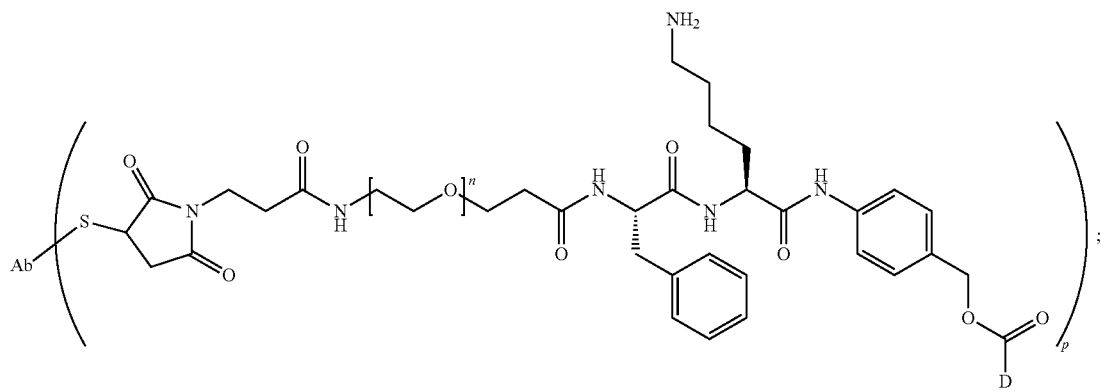
Phe-homoLys-PAB-Ab wherein n is 0 to 12. In some embodiments, n is 2 to 10. In some embodiments, n is 4 to 8.

Further nonlimiting exemplary ADCs include the structures:

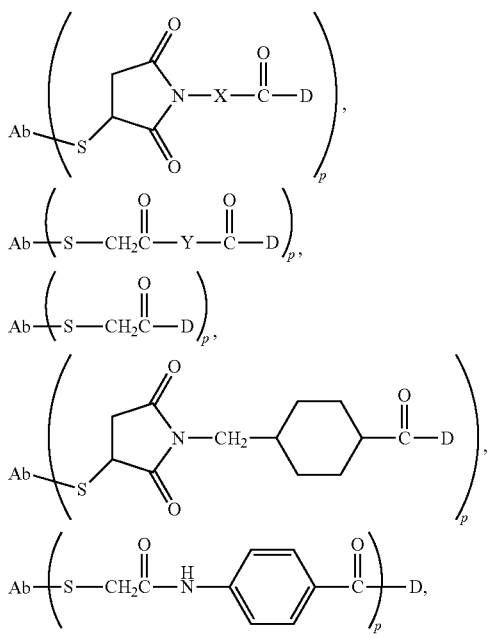

where X is:

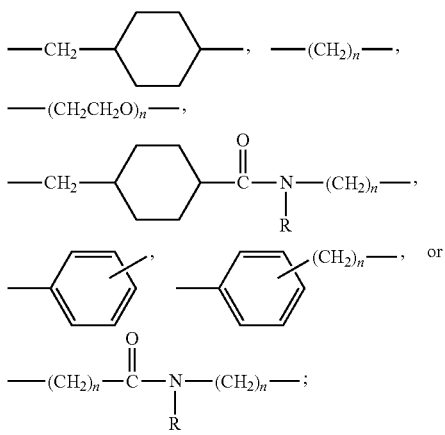

Y is:

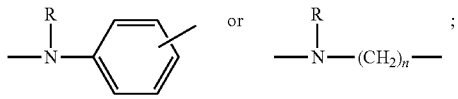

each R is independently H or $C_1$-$C_6$ alkyl; and n is 1 to 12.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), $BM(PEG)_2$ (shown below), and $BM(PEG)_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

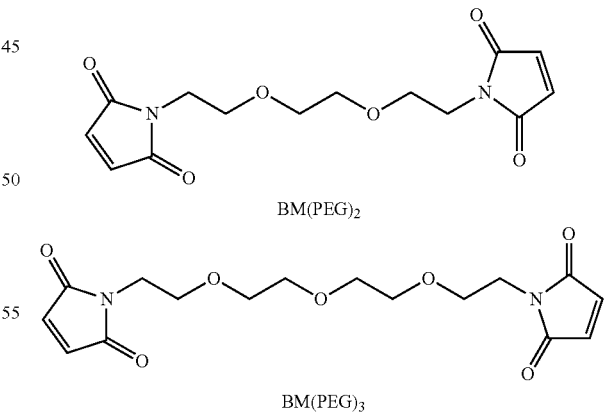

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.*

60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties

In some embodiments, an ADC comprises a pyrrolobenzodiazepine (PBD). In some embodiments, PBD dimers recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) *Chem. Rev.* 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

PBD dimers have been conjugated to antibodies and the resulting ADC shown to have anti-cancer properties. Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

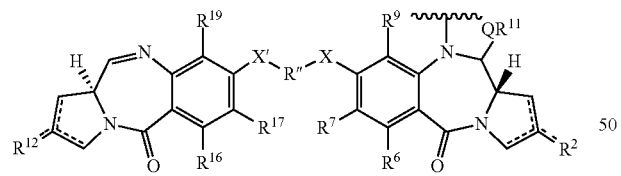

and salts and solvates thereof, wherein:
the wavy line indicates the covalent attachment site to the linker;
the dotted lines indicate the optional presence of a double bond between C1 and C2 or C2 and C3;
$R^2$ is independently selected from H, OH, =O, =$CH_2$, CN, R, OR, =CH—$R^D$, =C($R^D$)$_2$, O—$SO_2$—R, $CO_2R$ and COR, and optionally further selected from halo or dihalo, wherein $R^D$ is independently selected from R, $CO_2R$, COR, CHO, $CO_2H$, and halo;
$R^6$ and $R^9$ are independently selected from H, R, OH, OR, SH, SR, $NH_2$, NHR, NRR', $NO_2$, $Me_3Sn$ and halo;
$R^7$ is independently selected from H, R, OH, OR, SH, SR, $NH_2$, NHR, NRR', $NO_2$, $Me_3Sn$ and halo;

Q is independently selected from O, S and NH;
$R^{11}$ is either H, or R or, where Q is O, $SO_3M$, where M is a metal cation;
R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;
$R_{12}$, $R^{16}$, $R^{19}$ and $R^{17}$ are as defined for $R^2$, $R^6$, $R^9$ and $R^7$ respectively;
R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and
X and X' are independently selected from O, S and N(H).
In some embodiments, $R^9$ and $R^{19}$ are H.
In some embodiments, $R^6$ and $R^{16}$ are H.
In some embodiments, $R^7$ are $R^{17}$ are both $OR^{7A}$, where $R^{7A}$ is optionally substituted $C_{1-4}$ alkyl. In some embodiments, $R^{7A}$ is Me. In some embodiments, $R^{7A}$ is is $CH_2Ph$, where Ph is a phenyl group.
In some embodiments, X is O.
In some embodiments, $R^{11}$ is H.
In some embodiments, there is a double bond between C2 and C3 in each monomer unit.
In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-2}$ aryl or $C_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =$CH_2$, =CH—$R^D$, and =C($R^D$)$_2$. In some embodiments, $R^2$ and $R^{12}$ are each =$CH_2$. In some embodiments, $R^2$ and $R^{12}$ are each H. In some embodiments, $R^2$ and $R^{12}$ are each =O. In some embodiments, $R^2$ and $R^{12}$ are each =$CF_2$. In some embodiments, $R^2$ and/or $R^{12}$ are independently =C($R^D$)$_2$. In some embodiments, $R^2$ and/or $R^{12}$ are independently =CH—$R^D$.

In some embodiments, when $R^2$ and/or $R^{12}$ is =CH—$R^D$, each group may independently have either configuration shown below:

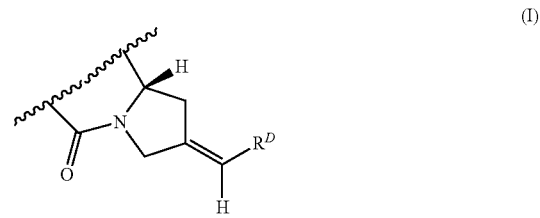

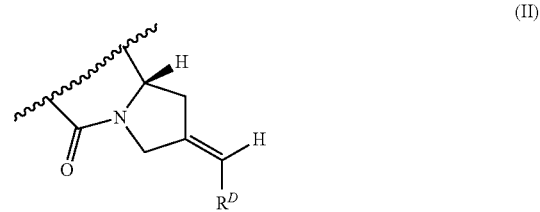

In some embodiments, a =CH—$R^D$ is in configuration (I).
In some embodiments, R" is a $C_3$ alkylene group or a $C_5$ alkylene group.

In some embodiments, an exemplary PBD dimer component of an ADC has the structure of Formula A(I):

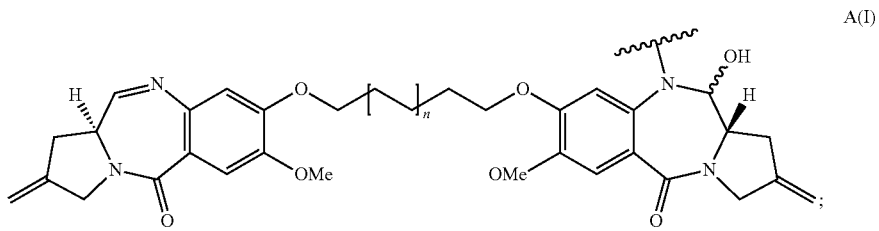

A(I)

wherein n is 0 or 1.

In some embodiments, an exemplary PBD dimer component of an ADC has the structure of Formula A(II):

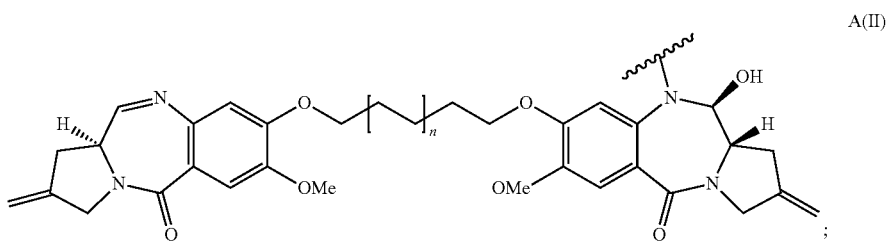

A(II)

wherein n is 0 or 1.

In some embodiments, an exemplary PBD dimer component of an ADC has the structure of Formula A(III):

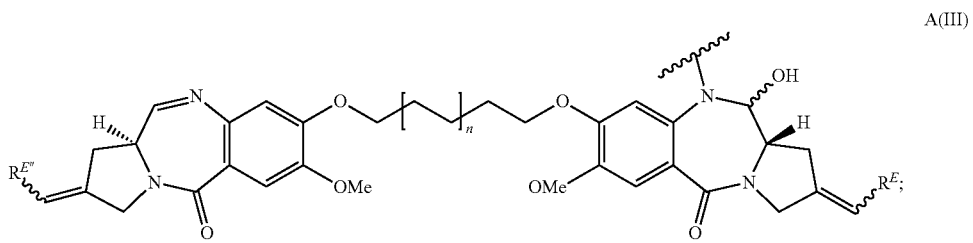

A(III)

wherein $R^E$ and $R^{E''}$ are each independently selected from H or $R^D$, wherein $R^D$ is defined as above; and wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

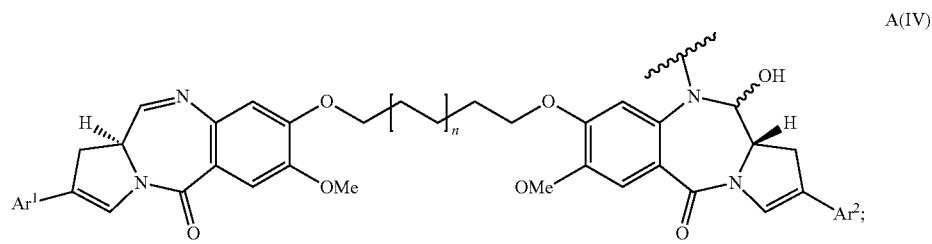

A(IV)

wherein Ar¹ and Ar² are each independently optionally substituted $C_{5-20}$ aryl; wherein Ar¹ and Ar² may be the same or different; and wherein n is 0 or 1.

In some embodiments, an exemplary PBD dimer component of an ADC has the structure of Formula A(V):

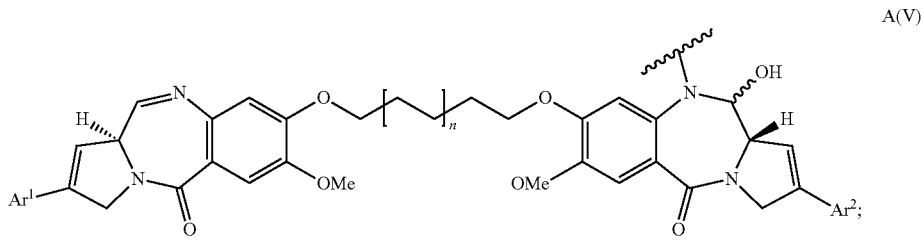

A(V)

wherein Ar¹ and Ar² are each independently optionally substituted $C_{5-20}$ aryl; wherein Ar¹ and Ar² may be the same or different; and wherein n is 0 or 1.

In some embodiments, Ar¹ and Ar² are each independently selected from optionally substituted phenyl, furanyl, thiophenyl and pyridyl. In some embodiments, Ar¹ and Ar² are each independently optionally substituted phenyl. In some embodiments, Ar¹ and Ar² are each independently optionally substituted thien-2-yl or thien-3-yl. In some embodiments, Ar¹ and Ar² are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

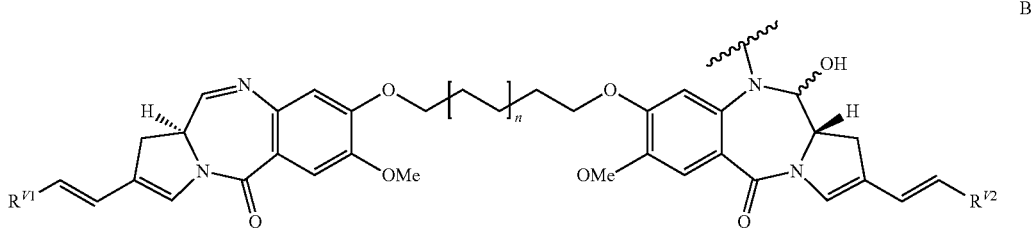

B and salts and solvates thereof, wherein:
the wavy line indicates the covalent attachment site to the linker;
the wavy line connected to the OH indicates the S or R configuration;
$R^{V1}$ and $R^{V2}$ are independently selected from H, methyl, ethyl, and phenyl (which phenyl may be optionally substituted with fluoro, particularly in the 4 position) and $C_{5-6}$ heterocyclyl; wherein $R^{V1}$ and $R^{V2}$ may be the same or different; and
n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

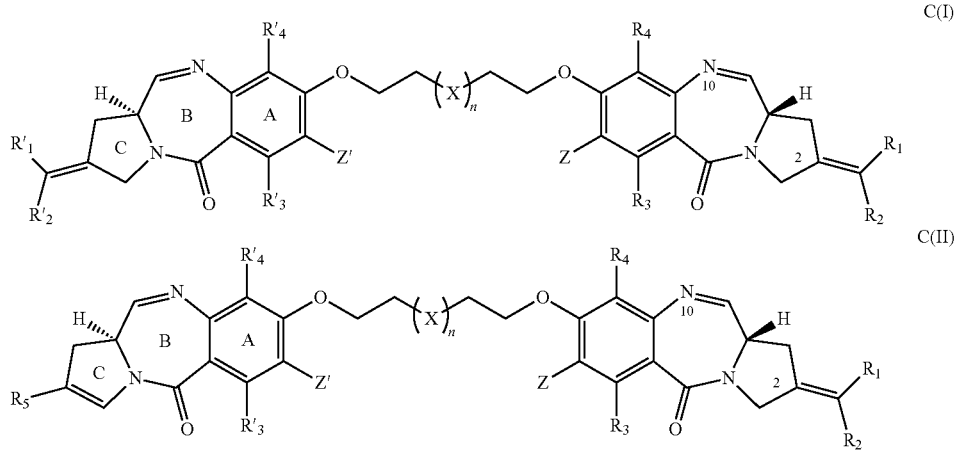

Formulas C(I) and C(II) are shown in their N10-C11 imine form. Exemplary PBD drug moieties also include the carbinolamine and protected carbinolamine forms as well, as shown in the table below:

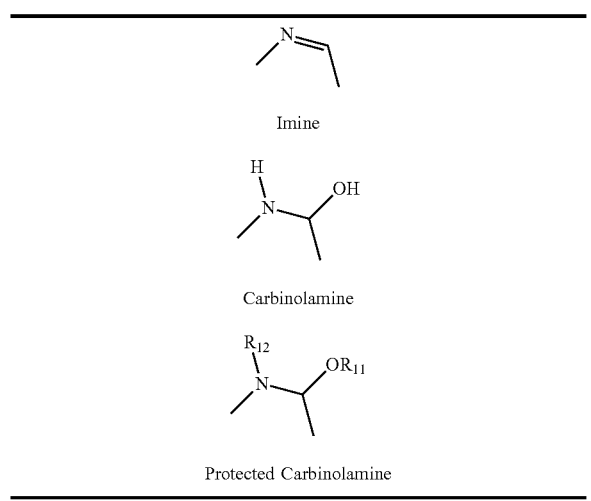

wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, $-NH_2$, $-NHMe$, $-OH$, and $-SH$, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is is H, $C_1$-$C_8$ alkyl, or a protecting group;

wherein a hydrogen of one of $R_1$, $R'_1$, $R_2$, $R'_2$, or $R_{12}$ or a hydrogen of the $-OCH_2CH_2(X)_nCH_2CH_2O-$ spacer between the A rings is replaced with a bond connected to the linker of the ADC.

Exemplary PBD dimer portions of ADC include, but are not limited to (the wavy line indicates the site of covalent attachment to the linker):

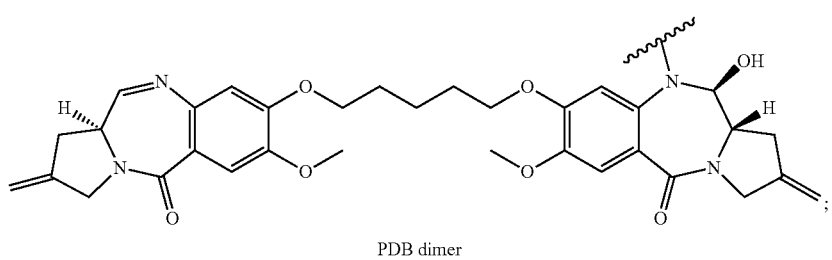

PDB dimer

Nonlimiting exemplary embodiments of ADCs comprising PBD dimers have the following structures:

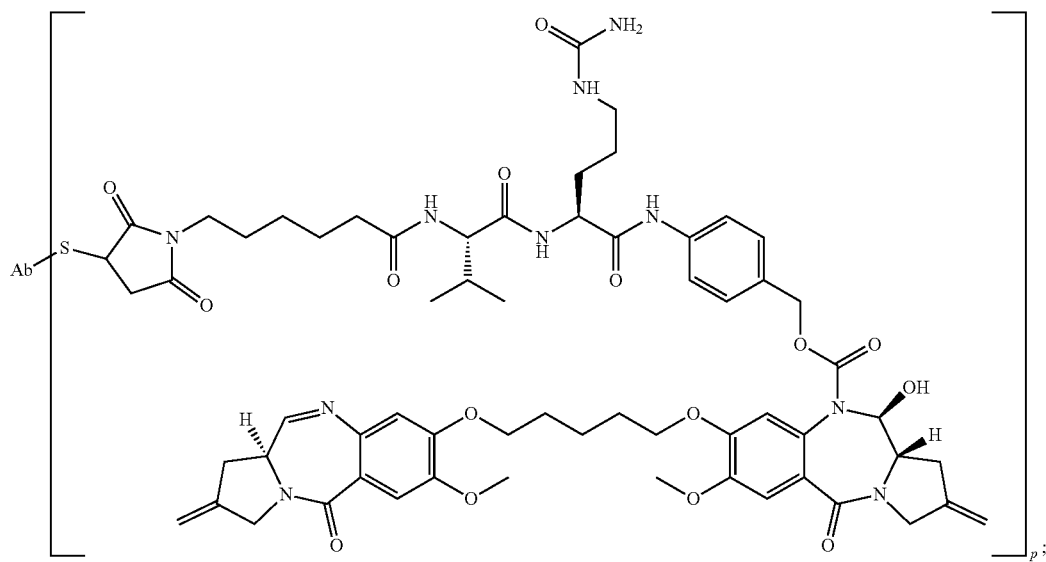
PBD dimer-val-cit-PAB-Ab

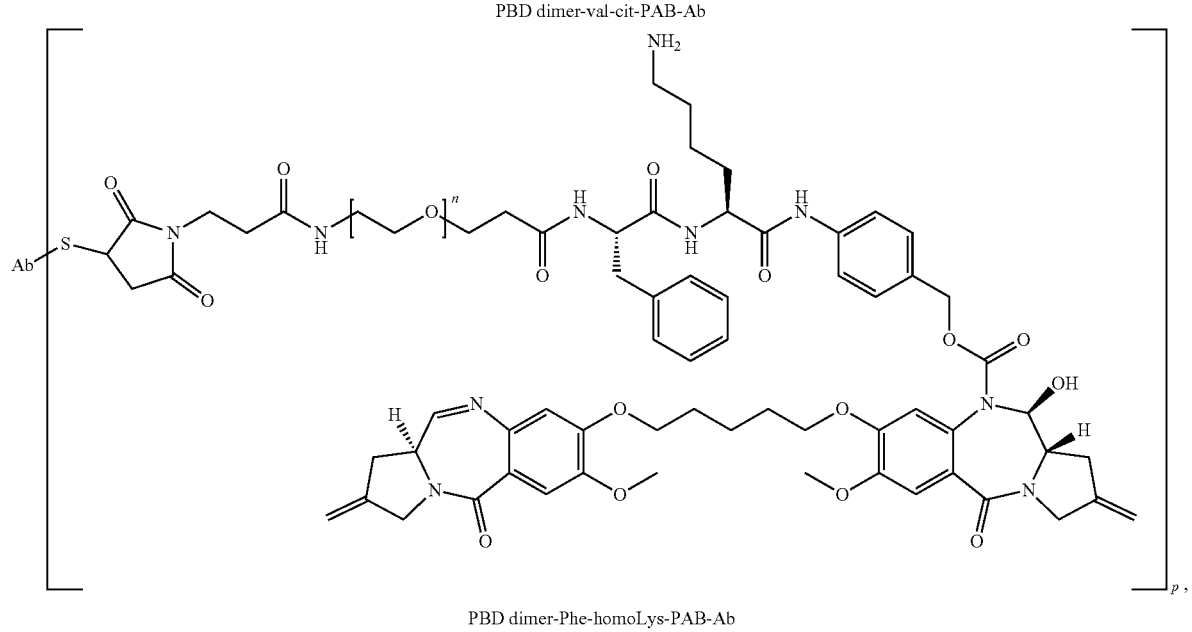
PBD dimer-Phe-homoLys-PAB-Ab wherein:

n is 0 to 12. In some embodiments, n is 2 to 10. In some embodiments, n is 4 to 8. In some embodiments, n is selected from 4, 5, 6, 7, and 8.

The linkers of PBD dimer-val-cit-PAB-Ab and the PBD dimer-Phe-homoLys-PAB-Ab are protease cleavable.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p >5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i)N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the anti-ETBR antibodies provided herein is useful for detecting the presence of ETBR in a biological sample. The term "detecting" as used herein encompasses quantitative or qualitative detection. A "biological sample" comprises, e.g., a cell or tissue (e.g., biopsy material, including cancerous or potentially cancerous skin tissue, including tissue from subjects having or suspected of having melanoma).

In one embodiment, an anti-ETBR antibody for use in a method of diagnosis or detection is provided. In a further aspect, a method of detecting the presence of ETBR in a biological sample is provided. In certain embodiments, the method comprises contacting the biological sample with an anti-ETBR antibody as described herein under conditions permissive for binding of the anti-ETBR antibody to ETBR, and detecting whether a complex is formed between the anti-ETBR antibody and ETBR in the biological sample. Such method may be an in vitro or in vivo method. In one embodiment, an anti-ETBR antibody is used to select subjects eligible for therapy with an anti-ETBR antibody, e.g. where ETBR is a biomarker for selection of patients. In a further embodiment, the biological sample is a cell or tissue (e.g., cancerous or potentially cancerous skin tissue, including tissue of subjects having or suspected of having melanoma).

In a further embodiment, an anti-ETBR antibody is used in vivo to detect, e.g., by in vivo imaging, an ETBR-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting an ETBR-positive cancer in a subject, the method comprising administering a labeled anti-ETBR antibody to a subject having or suspected of having an ETBR-positive cancer, and detecting the labeled anti-ETBR antibody in the subject, wherein detection of the labeled anti-ETBR antibody indicates an ETBR-positive cancer in the subject. In certain of such embodiments, the labeled anti-ETBR antibody comprises an anti-ETBR antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-ETBR antibody immobilized to a substrate with a biological sample to be tested for the presence of ETBR, exposing the substrate to a second anti-ETBR antibody, and detecting whether the second anti-ETBR is bound to a complex between the first anti-ETBR antibody and ETBR in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous skin tissue, including tissue from subjects having or suspected of having melanoma). In certain embodiments, the first or second anti-ETBR antibody is any of the antibodies described herein.

Exemplary disorders that may be diagnosed or detected according to any of the above embodiments include ETBR-positive cancers, such as ETBR-positive melanoma. In some embodiments, an ETBR-positive cancer is a cancer that receives an anti-ETBR immunohistochemistry (IHC) score greater than "0," which corresponds to very weak or no staining in >90% of tumor cells. In some embodiments, an ETBR-positive cancer expresses ETBR at a 1+, 2+ or 3+ level, wherein 1+ corresponds to weak staining in >50% of neoplastic cells, 2+ corresponds to moderate staining in >50% neoplastic cells, and 3+ corresponds to strong staining in >50% of neoplastic cells. In some embodiments, an ETBR-positive cancer is a cancer that expresses ETBR according to an in situ hybridization (ISH) assay. In some such embodiments, a scoring system similar to that used for IHC is used. In some embodiments, an ETBR-positive cancer is a cancer that expresses ETBR according to a reverse-transcriptase PCR (RT-PCR) assay that detects ETBR mRNA. In some embodiments, the RT-PCR is quantitative RT-PCR.

In certain embodiments, labeled anti-ETBR antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-ETBR antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-ETBR antibodies or immunoconjugates provided herein may be used in methods, e.g., therapeutic methods.

In one aspect, an anti-ETBR antibody or immunoconjugate provided herein is used in a method of inhibiting proliferation of an ETBR-positive cell, the method comprising exposing the cell to the anti-ETBR antibody or immunoconjugate under conditions permissive for binding of the anti-ETBR antibody or immunoconjugate to ETBRon the surface of the cell, thereby inhibiting the proliferation of the cell. In certain embodiments, the method is an in vitro or an in vivo method. In some embodiments, the cell is a melanoma cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-ETBR antibody or immunoconjugate for use as a medicament is provided. In further aspects, an anti-ETBR antibody or immunoconjugate for use in a method of treatment is provided. In certain embodiments, an anti-ETBR antibody or immunoconjugate for use in treating ETBR-positive cancer is provided. In certain embodiments, the invention provides an anti-ETBR antibody or immunoconjugate for use in a method of treating an individual having an ETBR-positive cancer, the method comprising administering to the individual an effective amount of the anti-ETBR antibody or immunoconjugate. In one such embodiment, the method further comprises administering to the individual an effective amount of at least one additional therapeutic agent, e.g., as described below.

In a further aspect, the invention provides for the use of an anti-ETBR antibody or immunoconjugate in the manufacture or preparation of a medicament. In one embodiment, the medicament is for treatment of ETBR-positive cancer. In a further embodiment, the medicament is for use in a method of treating ETBR-positive cancer, the method comprising administering to an individual having ETBR-positive cancer an effective amount of the medicament. In one such embodiment, the method further comprises administering to the individual an effective amount of at least one additional therapeutic agent, e.g., as described below.

In a further aspect, the invention provides a method for treating ETBR-positive cancer. In one embodiment, the method comprises administering to an individual having such ETBR-positive cancer an effective amount of an anti-ETBR antibody or immunoconjugate. In one such embodiment, the method further comprises administering to the individual an effective amount of at least one additional therapeutic agent, as described below.

AN ETBR-positive cancer according to any of the above embodiments may be, e.g., melanoma. In some embodiments, an ETBR-positive cancer is a cancer that receives an anti-ETBR immunohistochemistry (IHC) or in situ hybridization (ISH) score greater than "0," which corresponds to very weak or no staining in >90% of tumor cells. In another embodiment, an ETBR-positive cancer expresses ETBR at a 1+, 2+ or 3+ level, wherein 1+ corresponds to weak staining in >50% of neoplastic cells, 2+ corresponds to moderate staining in >50% neoplastic cells, and 3+ corresponds to strong staining in >50% of neoplastic cells. In some embodiments, an ETBR-positive cancer is a cancer that expresses ETBR according to a reverse-transcriptase PCR (RT-PCR) assay that detects ETBR mRNA. In some embodiments, the RT-PCR is quantitative RT-PCR.

In some embodiments, methods of treating an individual having an ETBR-positive cancer are provided, wherein the ETBR-positive cancer is resistant to a first therapeutic. In some embodiments, the method comprises administering to the individual an effective amount of an immunoconjugate comprising an antibody that binds to ETBR. In some embodiments, the ETBR-positive cancer is melanoma. In some embodiments, the first therapeutic comprises a first antibody that binds an antigen other than ETBR. In some embodiments, the first therapeutic is a first immunoconjugate comprising a first antibody that binds an antigen other than ETBR and a first cytotoxic agent. In some embodiments, the first antibody binds an antigen selected from melanocyte protein PMEL17, tyrosinase-related protein 1 (TYRP1), cytotoxic T lymphocyte antigen 4 (CTLA-4), and glycoprotein NMB (GPNMB). In some embodiments, the first antibody binds PMEL17. In some embodiments, the first cytotoxic agent and the cytotoxic agent of the immunoconjugate comprising an antibody that binds to ETBR are different. In some such embodiments, the first cytotoxic agent is MMAE and the cytotoxic agent of the immunoconjugate comprising an antibody that binds to ETBR is a pyrrolobenzodiazepine.

In some embodiments, the first antibody binds ETBR. In some such embodiments, the first cytotoxic agent is selected from MMAE, a calicheamicin, and a nemorubicin derivative and the cytotoxic agent of the immunoconjugate described herein is a pyrrolobenzodiazepine. In some embodiments, the first cytotoxic agent is MMAE and the cytotoxic agent of the immunoconjugate described herein is a pyrrolobenzodiazepine.

In some embodiments, methods of treating an individual with cancer are provided, wherein the cancer is resistant to a first therapeutic. In some embodiments, the first therapeutic is a first immunoconjugate comprising a first antibody linked to a first cytotoxic agent through a first linker. In some embodiments, a method of treating an individual with a cancer that is resistant to a first therapeutic (such as a first immunoconjugate) comprises administering a second immunoconjugate comprising a second antibody linked to a second cytotoxic agent through a second linker. In some embodiments, the first antibody and the second antibody bind to different antigens and the first cytotoxic agent and the second cytotoxic agents are the same or different. In some embodiments, the first antibody and the second antibody bind to different antigens that are present on at least some of the same cells. In some embodiments, the first antibody and the second antibody bind to different antigens and the first cytotoxic agent and the second cytotoxic agents are different. In some embodiments, the first antibody and the second antibody bind to the same antigens, and the first cytotoxic agent and the second cytotoxic agent are different. In any of the foregoing embodiments, the first linker and the second linker may be the same or different. In some embodiments, the first antibody and the second antibody bind to different antigens, the first and second linkers are different, and the first and second cytotoxic agents are different.

An "individual" according to any of the above embodiments may be a human.

In a further aspect, the invention provides pharmaceutical formulations comprising any of the anti-ETBR antibodies or immunoconjugate provided herein, e.g., for use in any of the above therapeutic methods. In one embodiment, a pharmaceutical formulation comprises any of the anti-ETBR antibodies or immunoconjugates provided herein and a pharmaceutically acceptable carrier. In another embodiment, a pharmaceutical formulation comprises any of the anti-ETBR antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent.

In some embodiments, methods of treating cancer comprise administering an immunoconjugate described herein in combination with a second immunoconjugate comprising an antibody that binds an antigen an antigen selected from melanocyte protein PMEL17, tyrosinase-related protein 1 (TYRP1), cytotoxic T lymphocyte antigen 4 (CTLA-4), and glycoprotein NMB (GPNMB). In some such embodiments, the cytotoxic agent of the second immunoconjugate is selected from MMAE, a calicheamicin, a nemorubicin derivative, and a pyrrolobenzodiazepine. In some such embodiments, the cytotoxic agent of the second immunoconjugate is selected from MMAE, a calicheamicin, and a nemorubicin derivative. In some embodiments, the cytotoxic agent of the second immunoconjugate is an MMAE. An exemplary MMAE structure is shown in FIG. 7A. The linker portion of the MMAE-containing immunoconjugate may be the MC-val-cit-PAB linker shown in FIG. 7A, or may be a different linker, such as any of those described herein. In some embodiments, the cytotoxic agent of the second immunoconjugate is a nemorubicin derivative. Non-limiting exemplary nemorubicin derivatives include PNU-159682, which may have a structure selected from:

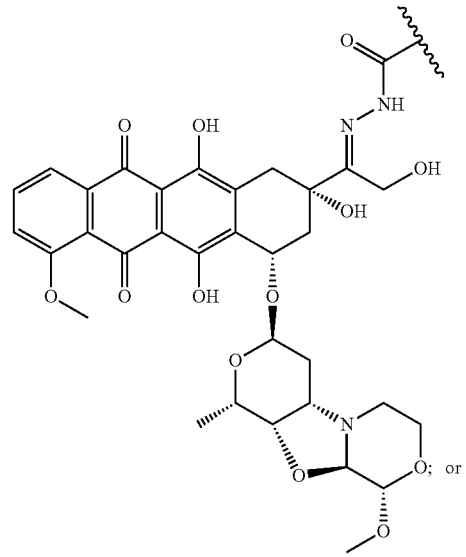

-continued

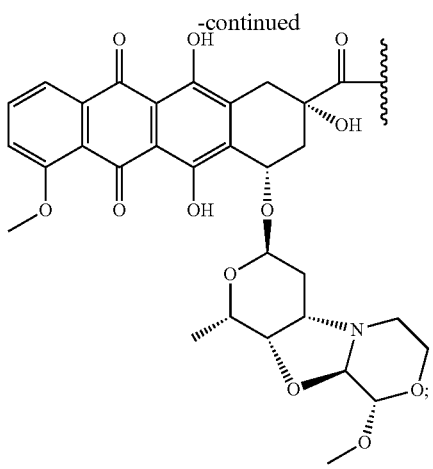

wherein the wavy line indicates the attachment to the linker (L). See, e.g., U.S. Publication No. 2011/0076287. The linker portion of the PNU-159682-containing immunoconjugate may, in some embodiments, be a linker described herein. In some embodiments, the linker comprises MC-val-cit-PAB, such as, for example, in the following structure:

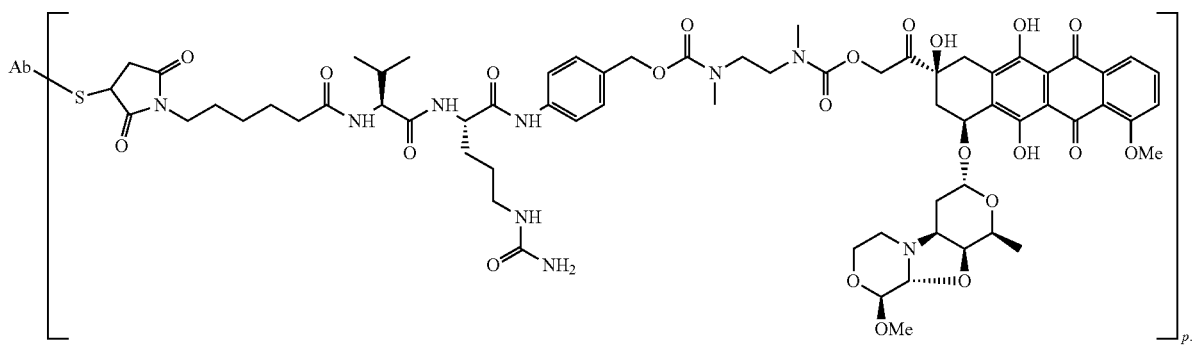

In some embodiments, methods of treating cancer comprise administering an immunoconjugate described herein in combination with a second immunoconjugate comprising an antibody that binds PMEL17. In some such embodiments, the cancer is an ETBR-positive cancer and also a PMEL17-positive cancer. Determination of whether a cancer is also PMEL17-positive may be carried out by any method, including, but not limited to, the methods described herein for determining whether a cancer is ETBR-positive, and methods described in U.S. Publication No. US 2011/0206702. In some embodiments, the antibody that binds PMEL17 comprises an HVR H1 comprising a sequence of SEQ ID NO: 21, an HVR H2 comprising a sequence of SEQ ID NO: 22, an HVR H3 comprising a sequence of SEQ ID NO: 23, an HVR L1 comprising a sequence of SEQ ID NO: 24, an HVR L2 comprising a sequence of SEQ ID NO: 25, and an HVR L3 comprising a sequence of SEQ ID NO: 26.

Administration "in combination" encompasses combined administration (where two or more therapeutic agents are included in the same or separate formulations), and separate administration, in which case, administration of the antibody or immunoconjugate of the invention can occur prior to, simultaneously, and/or following, administration of the additional therapeutic agent (such as the anti-PMEL17 immunoconjugate) and/or adjuvant. In some embodiments, administration of the anti-ETBR immunoconjugate and administration of an anti-PMEL17 immunoconjugate occur within about one month, or within about one, two, or three weeks, or within about one, two, three, four, five, or six days of one another. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-ETBR antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

A. Production of Anti-ETBR Antibody Drug Conjugates

Anti-ETBR antibody-drug conjugate (ADC) was produced by conjugating hu5E9.v1 (see, e.g., SEQ ID NOs: 5 and 6) or ch5E9 (see, e.g., SEQ ID NOs: 27 and 28) to the drug-linker moiety MC-vc-PAB-MMAE, which is depicted herein. For convenience, the drug-linker moiety MC-vc-PAB-MMAE is sometimes referred to in these Examples and in the Figures as "vcMMAE" or "VCE."

Prior to conjugation, the antibody was partially reduced with TCEP using standard methods in accordance with the methodology described in WO 2004/010957 A2. The partially reduced antibody was conjugated to the drug-linker moiety using standard methods in accordance with the methodology described, e.g., in Doronina et al. (2003) *Nat. Biotechnol.* 21:778-784 and US 2005/0238649 A1. Briefly, the partially reduced antibody was combined with the drug-linker moiety to allow conjugation of the drug-linker moiety to reduced cysteine residues of the antibody. The conjugation reaction was quenched by adding excess N-acetylcysteine to react with any free linker-drug moiety, and the ADC was purified. The structure of anti-ETBR-vc-MMAE (also referred to as anti-ETBR-MC-val-cit-PAB-MMAE) is shown in FIG. 7A. Anti-ETBR-vc-MMAE is also described, e.g., in U.S. Publication No. US 2011/0206702.

Anti-ETBR antibody drug conjugate (ADC) comprising a protease-cleavable val-cit linker and a PBD dimer drug are produced by conjugating ch5E9 to the drug-linker moiety MC-val-cit-PAB-PBD, substantially as described above. The structure of anti-ETBR-MC-val-cit-PAB-PBD is shown in FIG. 7B.

B. Efficacy of Anti-ETBR Immunoconjugates Comprising a Pyrrolobenzodiazepine in UACC-257X2.2 Melanoma Cells Resistant to Anti-ETBR-Vc-MMAE To determine the efficacy of an anti-ETBR immunoconjugate comprising a a pyrrolobenzodiazepine in melanoma that had developed resistance to anti-ETBR-vc-MMAE, UACC-257X2.2 melanoma cells that are resistant to anti-ETBR-vc-MMAE (also referred to as anti-EDNRB-vc-MMAE, anti-ETBR-MC-val-cit-PAB-MMAE, etc.; see, e.g., U.S. Publication No. US 2011/0206702) were developed in vivo and in vitro.

For resistance developed in vivo, NCr nude mice (Taconic, Hudson, N.Y.) were inoculated subcutaneously in the dorsal right flank with 5 million UACC-257X2.2 cells in HBSS with Matrigel. UACC-257X2.2 cells are derived from UACC-257 cells (National Cancer Institute) and optimized for growth in vivo as follows. UACC-257 cells were injected subcutaneously in the right flank of female NCr nude mice to induce tumor growth. One tumor was harvested and grown in vitro (referred to as UACC-257X1.2 cell line). The UACC-257X1.2 line was injected again subcutaneously in the right flank of female NCr nude mice to improve the growth of the cell line in vivo. A tumor from the second injection round was collected and again adapted for in vitro growth to generate UACC-257X2.2. The UACC-257X2.2 cell line and tumors derived from this line express ETBR at levels comparable to the parental cell line UACC-257.

Ten mice inoculated with UACC-257X2.2 cells were dosed with 3 mg/kg hu5E9.v1-MC-vc-PAB-MMAE intravenously on day 0. To determine when the mice would be dosed again, and at what doses, the following was taken into consideration: whether or not tumors re-grew after the initial treatment (i.e., tumors that grew back to initial tumor volume size at day 0), and the rate of re-growth. Frequency of doses administered varied over time but did not exceed 2 doses/week. Intravenous doses did not exceed 300 μL. The range of doses administered were 3 mg/kg, 6 mg/kg, 8 mg/kg, and 10 mg/kg. Dosing was discontinued once a tumor no longer responded (i.e., it showed resistance to) a series of increasing doses.

Figure 8:
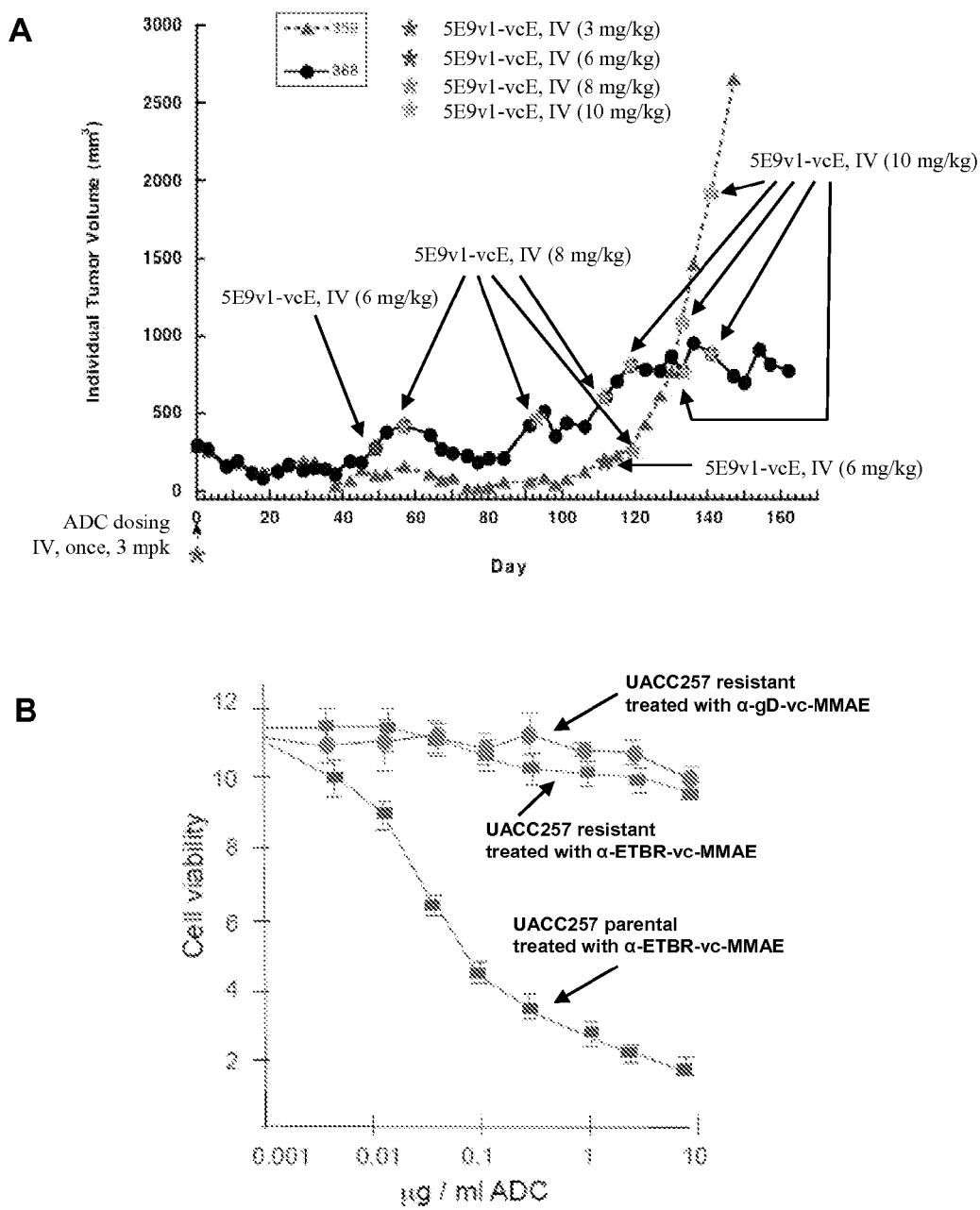
FIG. 8 shows (A) tumor volume over time in mice inoculated with UACC-257X2.2 melanoma cells and administered varying doses of anti-ETBR-vc-MMAE ("5E9v1-vcE"), and (B) parental and resistant UACC-257X2.2 cells grown in vitro in the presence of increasing concentrations of anti-ETBR-vc-MMAE ADC, as described in Example B.

As shown in FIG. 8A, the UACC-257X2.2 tumor #359 developed resistance to anti-ETBR-vc-MMAE after about 120 days, whereas tumor #368 developed resistance more slowly. Tumor #359 was harvested and the cells were dissociated for growth in vitro (referred to herein as in vivo-derived resistant UACC-257X2.2 cells).

For resistance developed in vitro, UACC-257X2.2 cells were adapted to increasing concentrations of anti-ETBR-vc-MMAE in culture dishes over the course of two months. FIG. 8B shows the resistant UACC-257X2.2 cell line derived in vitro (referred to herein as in vitro-derived resistant UACC-257X2.2 cells), which was relatively unaffected by concentrations of anti-ETBR-vc-MMAE up to at least 10 μg/ml. FIG. 8B also shows the in vitro-derived resistant UACC-257X2.2 cells incubated with a control ADC, α-gD-vc-MMAE, and the parental UACC-257X2.2 cells incubated with a-ETBR-vc-MMAE.

Expression of ETBR on the surface of the in vivo- and in vitro-derived resistant UACC-257X2.2 cells and the parental UACC-257X2.2 cells was then determined by FACS. Cells were stained with anti-ETBR antibody (ch5E9 or hu5E9.v1), followed by an anti-human Alexa 488 antibody conjugate. As shown in FIGS. 9A and B, both the in vivo-derived and in vitro-derived resistant UACC-257X2.2 cells had decreased expression of ETBR on the surface of the cells relative to the parental cell line. The control peak in each figure shows staining with secondary antibody only.

In vivo- and in vitro-derived resistant UACC-257X2.2 cells were then assayed for sensitivity to increasing concentrations of anti-ETBR-vc-MMAE.

In vitro cell proliferation of the cell lines in the presence of the immunoconjugates was assessed. Cells were plated at 1,500 cells per well in 50 μL of normal growth medium in 96-well clear-bottom plates. Twenty-four hours later, an additional 50 μL of culture medium with serial dilutions of immunoconjugates (ch5E9-vc-MMAE or control anti-gD-vc-MMAE) were added to triplicate wells. Five days later, cell survival was determined using CellTiter-Glo Luminescent Cell Viability Reagent (G7572, Promega Corporation, Madison, Wis.) using an EnVision 2101 Mutilabel Reader (Perkin-Elmer, Waltham, Mass.).

Table 2 shows the EC50 observed for anti-ETBR-vc-MMAE and linker-drug (without antibody) for each of the cell lines.

TABLE 2

EC50s of anti-ETBR-vc-MMAE in sensitive and resistant UACC-257X2.2 cells

| Cells | EC50 (anti-ETBR-vc-MMAE) | EC50 (free MC-vc-PAB-MMAE) |
|---|---|---|
| Parental UACC-257X2.2 | 45 ng/mL | 0.28 nM |
| In vivo-derived resistant UACC-257X2.2 | 235 ng/mL | 0.77 nM |
| In vitro-derived resistant UACC-257X2.2 | n.d.* | 3.5 nM |

*Cell killing by anti-ETBR-vc-MMAE was comparable to killing by a control ADC, anti-gD-vc-MMAE.

The results of this experiment suggest that at least some of the resistance is developed to the drug portion of the ADC, suggesting that replacing the drug with a different drug may restore some sensitivity in resistant cells.

To determine if some sensitivity can be restored by changing the drug portion of the ADC, the in vivo- and in vitro-derived resistant UACC-257X2.2 cells were assayed for sensitivity to an ADC with a different drug than was used to develop the resistant cells. The ADC tested in this experiment was anti-ETBR linked to a PBD dimer through a val-cit linker (ch5E9-vc-PBD). See FIG. 7B. Table 3 shows the EC50s observed for anti-ETBR-vc-PBD and linker-drug (without antibody) for each of the cell lines.

TABLE 3

EC50s of anti-ETBR-vc-PBD in sensitive and resistant UACC-257X2.2 cells

| Cells | EC50 (anti-ETBR-vc-PBD) | EC50 (free MC-vc-PAB-PBD) |
|---|---|---|
| Parental UACC-257X2.2 | 12 ng/mL | 6.2 nM |
| In vivo-derived resistant UACC-257X2.2 | 22 ng/mL | ND |
| In vitro-derived resistant UACC-257X2.2 | 64 ng/mL | 13.56 nM |

ND = not determined.

The results of this experiment demonstrate that at least some sensitivity can be restored in the resistant cells by replacing the drug portion of the ADC, e.g., with a PBD dimer.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Description | Sequence |
|---|---|---|
| 1 | mu5E9 light chain | DVVMTQTPLT LSVTIGQPAS ISCKSSQSLL DSDGKTYLNW LLQRPGQSPK RLIYLVSKLD SGVPDRFTGS GSGTDFTLKI TRVEAEDLGV YYCWQGTHFP YTFGGGTKLE IKRADAAPTV SIFPPSSEQL TSGGASVVCF LNNFYPKDIN VKWKIDGSER QNGVLNSWTD QDSKDSTYSM SSTLTLTKDE YERHNSYTCE ATHKTSTSPI VKSFNRNEC |
| 2 | mu5E9 heavy chain | QVQLLQSGAE LARPGASVKL SCKASGYTFT SYWMQWVKQR PGQGLEWIGT IYPGDGDTSY AQKFKGKATL TTDKYSSTAY MQLSSLASED SAVYYCARWG YAYDIDNWGQ GTTVTVSSAS TKGPSVYPLA PVCGDTTGSS VTLGCLVKGY FPEPVTLTWN SGSLSSGVHT FPAVLQSDLY TLSSSVTVTS STWPSQSITC NVAHPASSTK VDKKIEPRGP TIKPCPPCKC PAPNLLGGPS VFIFPPKIKD VLMISLSPIV TCVVVDVSED DPDVQISWFV NNVEVHTAQT QTHREDYNST |

| | | Table of Sequences |
|---|---|---|
| SEQ ID NO | Description | Sequence |
| | | LRVVSALPIQ HQDWMSGKEF KCKVNNKDLP APIERTISKP KGSVRAPQVY VLPPPEEEMT KKQVTLTCMV TDFMPEDIYV EWTNNGKTEL NYKNTEPVLD SDGSYFMYSK LRVEKKNWVE RNSYSCSVVH EGLHNHHTTK SFSRTPGK |
| 3 | mu5E9 light chain variable region | DVVMTQTPLT LSVTIGQPAS ISCKSSQSLL DSDGKTYLNW LLQRPGQSPK RLIYLVSKLD SGVPDRFTGS GSGTDFTLKI TRVEAEDLGV YYCWQGTHFP YTFGGGTKLE IK |
| 4 | mu5E9 heavy chain variable region | QVQLLQSGAE LARPGASVKL SCKASGYTFT SYWMQWVKQR PGQGLEWIGT IYPGDGDTSY AQKFKGKATL TTDKYSSTAY MQLSSLASED SAVYYCARWG YAYDIDNWG |
| 5 | hu5E9.v1 light chain | DIQMTQSPSS LSASVGDRVT ITCKSSQSLL DSDGKTYLNW LQQKPGKAPK RLIYLVSKLD SGVPSRFSGS GSGTDFTLTI SSLQPEDFAT YYCWQGTHFP YTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 6 | hu5E9.v1 heavy chain | EVQLVESGGG LVQPGGSLRL SCAASGYTFT SYWMQWVRQA PGKGLEWIGT IYPGDGDTSY AQKFKGRATL STDKSKNTAY LQMNSLRAED TAVYYCARWG YAYDIDNWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 7 | hu5E9.v1 light chain variable region | DIQMTQSPSS LSASVGDRVT ITCKSSQSLL DSDGKTYLNW LQQKPGKAPK RLIYLVSKLD SGVPSRFSGS GSGTDFTLTI SSLQPEDFAT YYCWQGTHFP YTFGQGTKVE IK |
| 8 | hu5E9.v1 heavy chain variable region | EVQLVESGGG LVQPGGSLRL SCAASGYTFT SYWMQWVRQA PGKGLEWIGT IYPGDGDTSY AQKFKGRATL STDKSKNTAY LQMNSLRAED TAVYYCARWG YAYDIDNWG |
| 9 | hu5E9.v2 heavy chain variable region | EVQLVQSGAE VKKPGASVKV SCKASGYTFT SYWMQWVRQA PGQGLEWIGT IYPGDGDTSY AQKFKGRVTI TRDTSTSTAY LELSSLRSED TAVYYCARWG YAYDIDNWG |
| 10 | Exemplary human endothelin B receptor protein | MQPPPSLCGR ALVALVLACG LSRIWGEERG FPPDRATPLL QTAEIMTPPT KTLWPKGSNA SLARSLAPAE VPKGDRTAGS PPRTISPPPC QGPIEIKETF KYINTVVSCL VFVLGIIGNS TLLRIIYKNK CMRNGPNILI ASLALGDLLH IVIDIPINVY KLLAEDWPFG AEMCKLVPFI QKASVGITVL SLCALSIDRY RAVASWSRIK GIGVPKWTAV EIVLIWVVSV VLAVPEAIGF DIITMDYKGS YLRICLLHPV QKTAFMQFYK TAKDWWLFSF YFCLPLAITA FFYTLMTCEM LRKKSGMQIA LNDHLKQRRE VAKTVFCLVL VFALCWLPLH LSRILKLTLY NQNDPNRCEL LSFLLVLDYI GINMASLNSC INPIALYLVS KRFKNCFKSC LCCWCQSFEE KQSLEEKQSC LKFKANDHGY DNFRSSNKYS SS |
| 11 | Exemplary human endothelin B receptor protein without signal sequence | EERGFPPDRA TPLLQTAEIM TPPTKTLWPK GSNASLARSL APAEVPKGDR TAGSPPRTIS PPPCQGPIEI KETFKYINTV VSCLVFVLGI IGNSTLLRII YKNKCMRNGP NILIASLALG DLLHIVIDIP INVYKLLAED WPFGAEMCKL VPFIQKASVG ITVLSLCALS IDRYRAVASW SRIKGIGVPK WTAVEIVLIW VVSVVLAVPE AIGFDIITMD YKGSYLRICL LHPVQKTAFM QFYKTAKDWW LFSFYFCLPL AITAFFYTLM TCEMLRKKSG MQIALNDHLK QRREVAKTVF CLVLVFALCW LPLHLSRILK LTLYNQNDPN RCELLSFLLV LDYIGINMAS LNSCINPIAL YLVSKRFKNC FKSCLCCWCQ SFEEKQSLEE KQSCLKFKAN DHGYDNFRSS NKYSSS |
| 12 | 5E9 HVR H1 | GYTFTSYWMQ |
| 13 | 5E9 HVR H2 | TIYPGDGDTSYAQKFKG |
| 14 | 5E9 HVR H3 | WGYAYDIDN |
| 15 | 5E9 HVR L1 | KSSQSLLDSDGKTYLN |
| 16 | 5E9 HVR L2 | LVSKLDS |
| 17 | 5E9 HVR L3 | WQGTHFPYT |
| 18 | hu5E9.v1 V205C cysteine | DIQMTQSPSS LSASVGDRVT ITCKSSQSLL DSDGKTYLNW LQQKPGKAPK RLIYLVSKLD SGVPSRFSGS GSGTDFTLTI SSLQPEDFAT YYCWQGTHFP YTFGQGTKVE IKRTVAAPSV FIFPPSDEQL KSGTASVVCL LNNFYPREAK |

Table of Sequences

| SEQ ID NO | Description | Sequence |
|---|---|---|
| | engineered light chain (Igκ) | VQWKVDNALQ SGNSQESVTE QDSKDSTYSL SSTLTLSKAD YEKHKVYACE VTHQGLSSPC TKSFNRGEC |
| 19 | hu5E9.v1 A118C cysteine engineered heavy chain (IgG1) | EVQLVESGGG LVQPGGSLRL SCAASGYTFT SYWMQWVRQA PGKGLEWIGT IYPGDGDTSY AQKFKGRATL STDKSKNTAY LQMNSLRAED TAVYYCARWG YAYDIDNWG QGTLVTVSS CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 20 | hu5E9.v1 S400C cysteine engineered heavy chain Fc region (IgG1) | EVQLVESGGG LVQPGGSLRL SCAASGYTFT SYWMQWVRQA PGKGLEWIGT IYPGDGDTSY AQKFKGRATL STDKSKNTAY LQMNSLRAED TAVYYCARWG YAYDIDNWG QGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDCDGSFFLY SKLTVDKSRW QQGNVFSCSV MHEALHNHYT QKSLSLSPGK |
| 21 | 17A9 HVR H1 | GYSFTRYTMN |
| 22 | 17A9 HVR H2 | VINPYNGGTVYNQKFKG |
| 23 | 17A9 HVR H3 | TDYDGYAMDY |
| 24 | 17A9 HVR L2 | SGSTLQS |
| 25 | 17A9 HVR L3 | QQHNEYPYT |
| 26 | 17A9 HVR L2 | SGSTLQS |
| 27 | ch5E9 light chain | DVVMTQTPLT LSVTIGQPAS ISCKSSQSLL DSDGKTYLNW LLQRPGQSPK RLIYLVSKLD SGVPDRFTGS GSGTDFTLKI TRVEAEDLGV YYCWQGTHFP YTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 28 | ch5E9 heavy chain | QVQLLQSGAE LARPGASVKL SCKASGYTFT SYWMQWVKQR PGQGLEWIGT IYPGDGDTSY AQKFKGKATL TTDKYSSTAY MQLSSLASED SAVYYCARWG YAYDIDNWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |

What is claimed is:

1. A method of treating an individual having an ETBR-positive cancer, wherein the ETBR-positive cancer is resistant to a first immunoconjugate comprising a first antibody that binds ETBR and a first cytotoxic agent which is an auristatin, the method comprising administering to the individual an effective amount of an immunoconjugate comprising an antibody that binds ETBR covalently attached to a cytotoxic agent, wherein the antibody binds an epitope within amino acids 64 to 101 of SEQ ID NO: 10, and wherein the cytotoxic agent is a pyrrolobenzodiazepine.

2. The method of claim 1, wherein the first cytotoxic agent is MMAE.

3. The method of claim 1, wherein the antibody that is administered comprises (i) HVR-H1 comprising the amino acid sequence of SEQ ID NO: 12, (ii) HVR-H2 comprising the amino acid sequence of SEQ ID NO: 13, (iii) HVR-H3 comprising the amino acid sequence of SEQ ID NO: 14, (iv) HVR-L1 comprising the amino acid sequence of SEQ ID NO: 15, (v) HVR-L2 comprising the amino acid sequence of SEQ ID NO: 16, and (vi) HVR-L3 comprising the amino acid sequence of SEQ ID NO: 17.

4. The method of claim 3, wherein the antibody that is administered comprises:

a) a VH sequence having at least 95% sequence identity to the amino acid sequence of SEQ ID NO: 8; or b) a VL sequence having at least 95% sequence identity to the amino acid sequence of SEQ ID NO: 7; or c) a VH sequence as in (a) and a VL sequence as in (b).

5. The method of claim 4, comprising a VH sequence having the amino acid sequence of SEQ ID NO: 8 or SEQ ID NO: 9.

6. The method of claim 4, comprising a VL sequence having the amino acid sequence of SEQ ID NO: 7.

7. The method of claim 1,
wherein the antibody that is administered is an IgG1, IgG2a or IgG2b antibody.

8. The method of claim 1, wherein the immunoconjugate that is administered has the formula Ab-(L-D)p, wherein:

(a) Ab is the antibody;

(b) L is a linker;

(c) D is the cytotoxic agent; and (d) p ranges from 1-8.

9. The method of claim 8, wherein D is a pyrrolobenzodiazepine of Formula A:

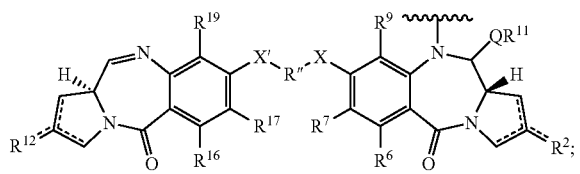

A wherein the wavy line indicates the covalent attachement site to the linker; the dotted lines indicate the optional presence of a double bond between C1 and C2 or C2 and C3;

$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-12}$ alkyl, C$_{3-20}$ heterocyclyl and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms and/or aromatic rings that are optionally substituted; and X and X' are independently selected from O, S and N(H).

10. The immunoconjugate of claim 9, wherein D has the structure:

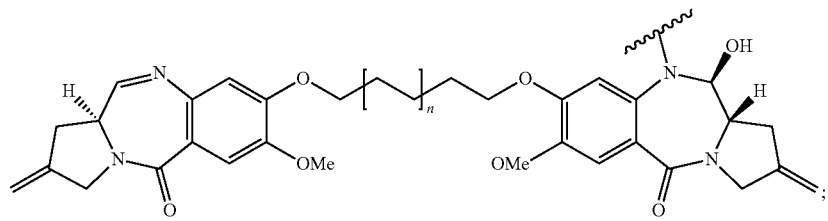

A(II)

wherein n is 0 or 1.

11. The method of claim 9, wherein D has a structure selected from:

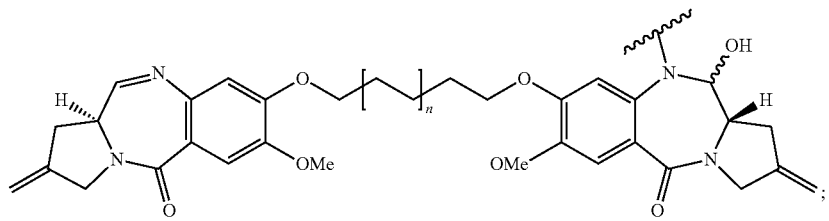

A(I)

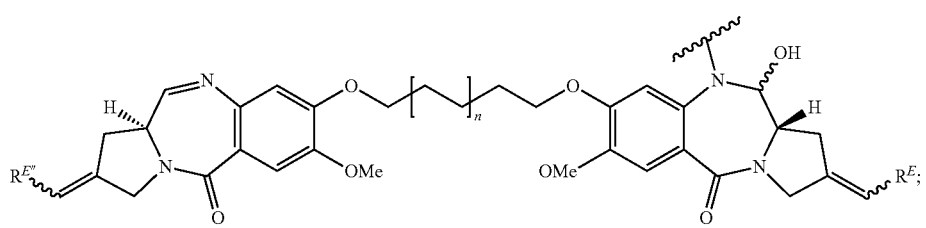

A(III)

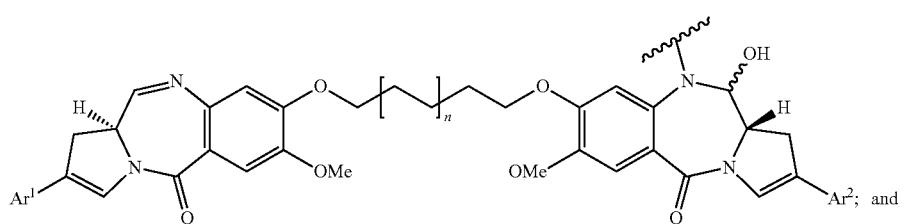

A(IV)

-continued

A(V)

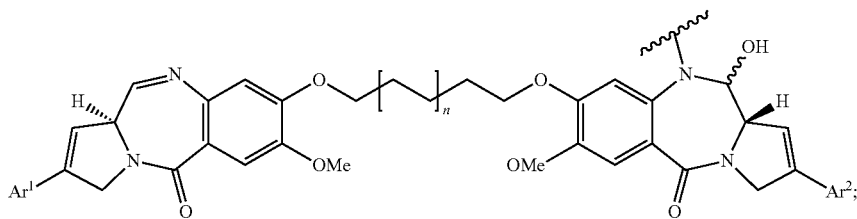

wherein $R^E$ and $R^{E''}$ are each independently selected from H or $R^D$, wherein $R^D$ is independently selected from R, $CO_2R$, COR, CHO, $CO_2H$, and halo;
wherein $Ar^1$ and $Ar^2$ are each independently optionally substituted $C_{5-20}$ aryl; and
wherein n is 0 or 1.

12. The method of claim 8, wherein D is a pyrrolobenzodiazepine of Formula B:

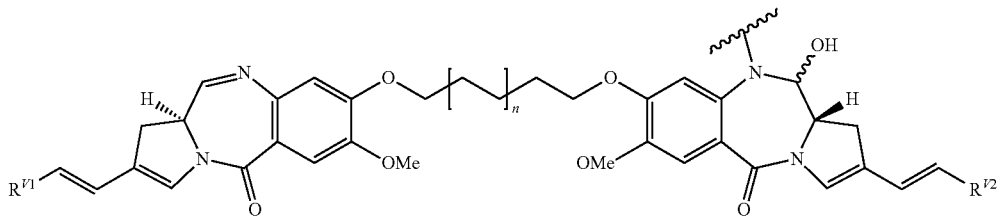

wherein the horizontal wavy line indicates the covalent attachement site to the linker;
$R^{v1}$ and $R^{V2}$ are independently selected from H, methyl, ethyl, phenyl, fluoro-substituted phenyl, and $C_{5-6}$ heterocyclyl; and
n is 0 or 1.

13. The method of claim 8, wherein the linker is cleavable by a protease.

14. The method of claim 13, wherein the linker comprises a valine-citrulline dipeptide, an N-methyl-valine-citrulline dipeptide, an alanine-phenylalanine dipeptide, a phenylalanine-lysine dipeptide, or a phenylalanine-homolysine dipeptide.

15. The method of claim 8 having the formula

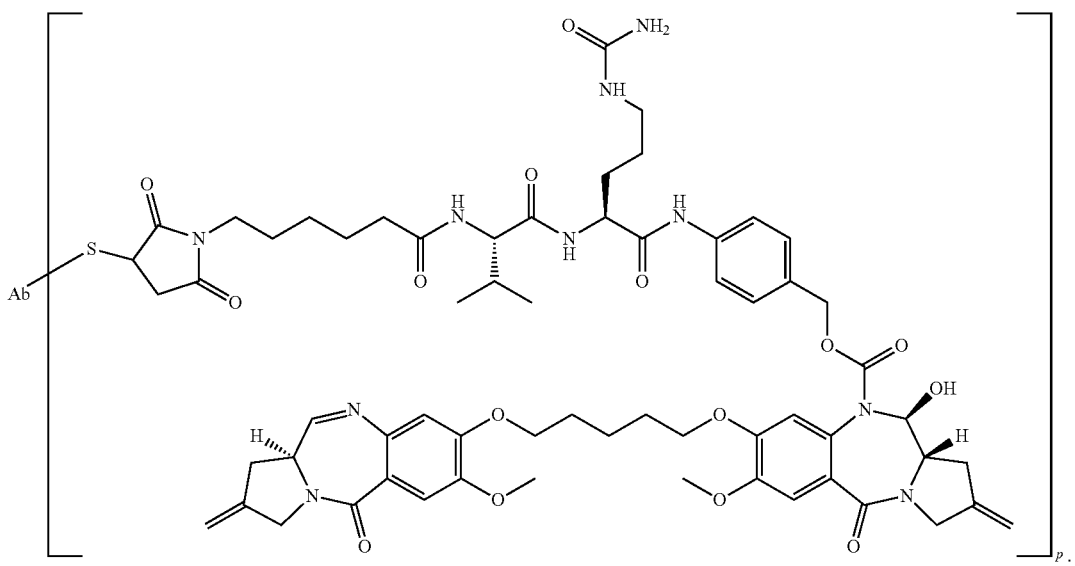

16. The method of claim 8, wherein p ranges from 1-3.

17. The method of claim 1, wherein the antibody that is administered is a monoclonal antibody.

18. The method of claim 1, wherein the antibody that is administered is a human, humanized, or chimeric antibody.

19. The method of claim 1, wherein the antibody that is administered is an antibody fragment that binds ETBR.

20. The method of claim 1, wherein the antibody that is administered binds human ETBR.

21. The method of claim 20, wherein human ETBR has the sequence of SEQ ID NO: 10 or SEQ ID NO: 11.

22. The method of claim 1, wherein the immunoconjugate is administered in a pharmaceutical formulation comprising the immunoconjugate of claim 1 and a pharmaceutically acceptable carrier.

23. The method of claim 22, wherein the pharmaceutical formulation further comprises an additional therapeutic agent.

24. A method of treating an individual having an ETBR-positive cancer, wherein the ETBR-positive cancer is resistant to a first immunoconjugate comprising a first antibody that binds ETBR and a cytotoxic agent which is an auristatin, the method comprising administering to the individual an effective amount of an immunoconjugate comprising an antibody that binds ETBR covalently attached to a cytotoxic agent, wherein the antibody comprises (a) a VH sequence having the amino acid sequence of SEQ ID NO: 8 and a VL sequence having the amino acid sequence of SEQ ID NO: 7, and wherein the cytotoxic agent is a pyrrolobenzodiazepine.

25. A method of treating an individual having an ETBR-positive cancer, wherein the ETBR-positive cancer is resistant to a first immunoconjugate comprising a first antibody that binds ETBR and a cytotoxic agent which is an auristatin, the method comprising administering to the individual an effective amount of an immunoconjugate having the formula:

the amino acid sequence of SEQ ID NO: 15, (v) HVR-L2 comprising the amino acid sequence of SEQ ID NO: 16, and (vi) HVR-L3 comprising the amino acid sequence of SEQ ID NO: 17; and wherein p ranges from 1 to 3.

26. The method of claim 25, wherein the antibody that is administered comprises a VH sequence of SEQ ID NO: 8 and a VL sequence of SEQ ID NO: 7.

27. The method of claim 26, wherein the antibody that is administered comprises a heavy chain of SEQ ID NO: 6 and a light chain of SEQ ID NO: 5.

28. A method of inhibiting proliferation of an ETBR-positive cell that is resistant to a first immunoconjugate comprising a first antibody that binds ETBR and a cytotoxic agent which is an auristatin, the method comprising exposing the cell to an immunoconjugate comprising a pyrrolobenzodiazepine covalently attached to an antibody that binds ETBR within amino acids 64 to 101 of SEQ ID NO: 10, under conditions permissive for binding of the immunoconjugate to ETBR on the surface of the cell, thereby inhibiting proliferation of the cell.

29. A method of treating an individual with ETBR-positive cancer, comprising administering to the individual an effective amount of a first immunoconjugate comprising an antibody that binds ETBR covalently attached to a cytotoxic agent, wherein the antibody binds an epitope within amino acids 64 to 101 of SEQ ID NO: 10, and wherein the cytotoxic agent is a pyrrolobenzodiazepine in combination with a second immunoconjugate comprising an antibody that binds PMEL17, wherein the ETBR-positive cancer is resistant to an immunoconjugate comprising an antibody that binds ETBR and a cytotoxic agent which is an auristatin.

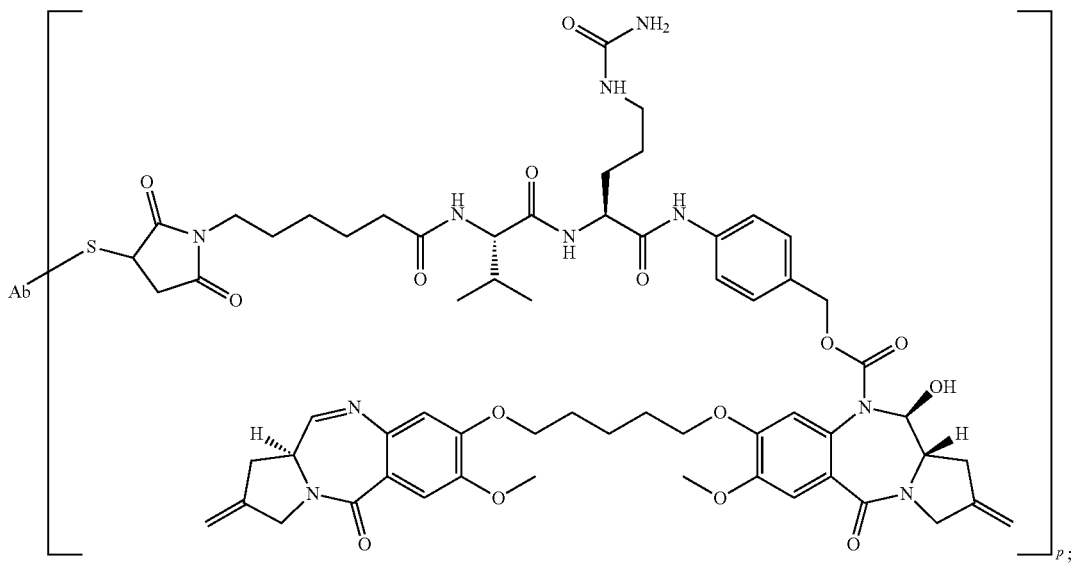

wherein Ab is an antibody comprising (i) HVR-H1 comprising the amino acid sequence of SEQ ID NO: 12, (ii) HVR-H2 comprising the amino acid sequence of SEQ ID NO: 13, (iii) HVR-H3 comprising the amino acid sequence of SEQ ID NO: 14, (iv) HVR-L1 comprising 30. The method of claim 29, wherein the second immunoconjugate comprises a cytotoxic agent selected from a pyrrolobenzodiazepine and a nemorubicin derivative.

* * * * *

SEQUENCE LISTING

<160> NUMBER OF SEQ ID NOS: 28

<210> SEQ ID NO 1
<211> LENGTH: 219
<212> TYPE: PRT
<213> ORGANISM: Artificial sequence
<220> FEATURE:
<223> OTHER INFORMATION: Synthetic

<400> SEQUENCE: 1

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

```
Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Thr Arg Val Glu Ala Glu Asp Leu Gly Val Tyr Tyr Cys Trp Gln Gly
                 85                  90                  95

Thr His Phe Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215

<210> SEQ ID NO 2
<211> LENGTH: 448
<212> TYPE: PRT
<213> ORGANISM: Artificial sequence
<220> FEATURE:
<223> OTHER INFORMATION: Synthetic

<400> SEQUENCE: 2

Gln Val Gln Leu Leu Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
             20                  25                  30

Trp Met Gln Trp Val Lys Gln Arg Pro Gly Gln Gly Leu Glu Trp Ile
         35                  40                  45

Gly Thr Ile Tyr Pro Gly Asp Gly Asp Thr Ser Tyr Ala Gln Lys Phe
     50                  55                  60

Lys Gly Lys Ala Thr Leu Thr Thr Asp Lys Ser Ser Ser Thr Ala Tyr
65                  70                  75                  80

Met Gln Leu Ser Ser Leu Ala Ser Glu Asp Ser Ala Val Tyr Tyr Cys
                 85                  90                  95

Ala Arg Trp Gly Tyr Ala Tyr Asp Ile Asp Asn Trp Gly Gln Gly Thr
            100                 105                 110

Thr Val Thr Val Ser Ser Ala Ser Thr Lys Gly Pro Ser Val Tyr Pro
            115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175
```

```
Ser Asp Leu Tyr Thr Leu Ser Ser Val Thr Val Thr Ser Ser Thr
                180                 185                 190

Trp Pro Ser Gln Ser Ile Thr Cys Asn Val Ala His Pro Ala Ser Ser
            195                 200                 205

Thr Lys Val Asp Lys Lys Ile Glu Pro Arg Gly Pro Thr Ile Lys Pro
        210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
                260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
        290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 3
<211> LENGTH: 112
<212> TYPE: PRT
<213> ORGANISM: Artificial sequence
<220> FEATURE:
<223> OTHER INFORMATION: Synthetic

<400> SEQUENCE: 3

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Thr Arg Val Glu Ala Glu Asp Leu Gly Val Tyr Tyr Cys Trp Gln Gly
                85                  90                  95
```

```
Thr His Phe Pro Tyr Thr Phe Gly Gly Gly Thr Lys Leu Glu Ile Lys
            100                 105                 110
```

<210> SEQ ID NO 4
<211> LENGTH: 109
<212> TYPE: PRT
<213> ORGANISM: Artificial sequence
<220> FEATURE:
<223> OTHER INFORMATION: Synthetic

<400> SEQUENCE: 4

```
Gln Val Gln Leu Leu Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Ser Tyr Ala Gln Lys Phe
    50                  55                  60

Lys Gly Lys Ala Thr Leu Thr Thr Asp Lys Tyr Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Trp Gly Tyr Ala Tyr Asp Ile Asp Asn Trp Gly
            100                 105
```

<210> SEQ ID NO 5
<211> LENGTH: 219
<212> TYPE: PRT
<213> ORGANISM: Artificial sequence
<220> FEATURE:
<223> OTHER INFORMATION: Synthetic

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Asp Gly Lys Thr Tyr Leu Asn Trp Leu Gln Gln Lys Pro Gly Lys Ala
        35                  40                  45

Pro Lys Arg Leu Ile Tyr Leu Val Ser Lys Leu Asp Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Trp Gln Gly
                85                  90                  95

Thr His Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 6
<211> LENGTH: 448
<212> TYPE: PRT
<213> ORGANISM: Artificial sequence
<220> FEATURE:
<223> OTHER INFORMATION: Synthetic

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met Gln Trp Val Arg Gln Ala Pro Gly Lys Gly Leu Glu Trp Ile
        35                  40                  45

Gly Thr Ile Tyr Pro Gly Asp Gly Asp Thr Ser Tyr Ala Gln Lys Phe
    50                  55                  60

Lys Gly Arg Ala Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly Tyr Ala Tyr Asp Ile Asp Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 7
<211> LENGTH: 112
<212> TYPE: PRT
<213> ORGANISM: Artificial sequence
<220> FEATURE:
<223> OTHER INFORMATION: Synthetic

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Asp Gly Lys Thr Tyr Leu Asn Trp Leu Gln Gln Lys Pro Gly Lys Ala
        35                  40                  45

Pro Lys Arg Leu Ile Tyr Leu Val Ser Lys Leu Asp Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Trp Gln Gly
                85                  90                  95

Thr His Phe Pro Tyr Thr Phe Gly Gln Gly Thr Lys Val Glu Ile Lys
            100                 105                 110

<210> SEQ ID NO 8
<211> LENGTH: 109
<212> TYPE: PRT
<213> ORGANISM: Artificial sequence
<220> FEATURE:
<223> OTHER INFORMATION: Synthetic

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met Gln Trp Val Arg Gln Ala Pro Gly Lys Gly Leu Glu Trp Ile
        35                  40                  45

Gly Thr Ile Tyr Pro Gly Asp Gly Asp Thr Ser Tyr Ala Gln Lys Phe
    50                  55                  60

Lys Gly Arg Ala Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95

Ala Arg Trp Gly Tyr Ala Tyr Asp Ile Asp Asn Trp Gly
            100                 105

<210> SEQ ID NO 9
<211> LENGTH: 109
<212> TYPE: PRT
<213> ORGANISM: Artificial sequence
<220> FEATURE:
<223> OTHER INFORMATION: Synthetic

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Ile
        35                  40                  45

Gly Thr Ile Tyr Pro Gly Asp Gly Asp Thr Ser Tyr Ala Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Trp Gly Tyr Ala Tyr Asp Ile Asp Asn Trp Gly
            100                 105

<210> SEQ ID NO 10
<211> LENGTH: 442
<212> TYPE: PRT
<213> ORGANISM: Homo sapiens

<400> SEQUENCE: 10

Met Gln Pro Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Arg Ile Ile Tyr Lys
        115                 120                 125

Asn Lys Cys Met Arg Asn Gly Pro Asn Ile Leu Ile Ala Ser Leu Ala
    130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
            180                 185                 190
```

```
Cys Ala Leu Ser Ile Asp Arg Tyr Arg Ala Val Ala Ser Trp Ser Arg
            195                 200                 205

Ile Lys Gly Ile Gly Val Pro Lys Trp Thr Ala Val Glu Ile Val Leu
        210                 215                 220

Ile Trp Val Val Ser Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
            260                 265                 270

Lys Asp Trp Trp Leu Phe Ser Phe Tyr Phe Cys Leu Pro Leu Ala Ile
        275                 280                 285

Thr Ala Phe Phe Tyr Thr Leu Met Thr Cys Glu Met Leu Arg Lys Lys
290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
            340                 345                 350

Asn Asp Pro Asn Arg Cys Glu Leu Leu Ser Phe Leu Leu Val Leu Asp
        355                 360                 365

Tyr Ile Gly Ile Asn Met Ala Ser Leu Asn Ser Cys Ile Asn Pro Ile
370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
            420                 425                 430

Phe Arg Ser Ser Asn Lys Tyr Ser Ser
        435                 440

<210> SEQ ID NO 11
<211> LENGTH: 416
<212> TYPE: PRT
<213> ORGANISM: Homo sapiens

<400> SEQUENCE: 11

Glu Glu Arg Gly Phe Pro Pro Asp Arg Ala Thr Pro Leu Leu Gln Thr
1               5                   10                  15

Ala Glu Ile Met Thr Pro Pro Thr Lys Thr Leu Trp Pro Lys Gly Ser
            20                  25                  30

Asn Ala Ser Leu Ala Arg Ser Leu Ala Pro Ala Glu Val Pro Lys Gly
        35                  40                  45

Asp Arg Thr Ala Gly Ser Pro Arg Thr Ile Ser Pro Pro Cys
50                  55                  60

Gln Gly Pro Ile Glu Ile Lys Glu Thr Phe Lys Tyr Ile Asn Thr Val
65                  70                  75                  80

Val Ser Cys Leu Val Phe Val Leu Gly Ile Ile Gly Asn Ser Thr Leu
                85                  90                  95

Leu Arg Ile Ile Tyr Lys Asn Lys Cys Met Arg Asn Gly Pro Asn Ile
            100                 105                 110

Leu Ile Ala Ser Leu Ala Leu Gly Asp Leu Leu His Ile Val Ile Asp
```

```
            115                 120                 125
Ile Pro Ile Asn Val Tyr Lys Leu Leu Ala Glu Asp Trp Pro Phe Gly
    130                 135                 140

Ala Glu Met Cys Lys Leu Val Pro Phe Ile Gln Lys Ala Ser Val Gly
145                 150                 155                 160

Ile Thr Val Leu Ser Leu Cys Ala Leu Ser Ile Asp Arg Tyr Arg Ala
                165                 170                 175

Val Ala Ser Trp Ser Arg Ile Lys Gly Ile Gly Val Pro Lys Trp Thr
            180                 185                 190

Ala Val Glu Ile Val Leu Ile Trp Val Val Ser Val Val Leu Ala Val
        195                 200                 205

Pro Glu Ala Ile Gly Phe Asp Ile Ile Thr Met Asp Tyr Lys Gly Ser
    210                 215                 220

Tyr Leu Arg Ile Cys Leu Leu His Pro Val Gln Lys Thr Ala Phe Met
225                 230                 235                 240

Gln Phe Tyr Lys Thr Ala Lys Asp Trp Trp Leu Phe Ser Phe Tyr Phe
                245                 250                 255

Cys Leu Pro Leu Ala Ile Thr Ala Phe Phe Tyr Thr Leu Met Thr Cys
                260                 265                 270

Glu Met Leu Arg Lys Lys Ser Gly Met Gln Ile Ala Leu Asn Asp His
            275                 280                 285

Leu Lys Gln Arg Arg Glu Val Ala Lys Thr Val Phe Cys Leu Val Leu
        290                 295                 300

Val Phe Ala Leu Cys Trp Leu Pro Leu His Leu Ser Arg Ile Leu Lys
305                 310                 315                 320

Leu Thr Leu Tyr Asn Gln Asn Asp Pro Asn Arg Cys Glu Leu Leu Ser
                325                 330                 335

Phe Leu Leu Val Leu Asp Tyr Ile Gly Ile Asn Met Ala Ser Leu Asn
                340                 345                 350

Ser Cys Ile Asn Pro Ile Ala Leu Tyr Leu Val Ser Lys Arg Phe Lys
            355                 360                 365

Asn Cys Phe Lys Ser Cys Leu Cys Cys Trp Cys Gln Ser Phe Glu Glu
        370                 375                 380

Lys Gln Ser Leu Glu Glu Lys Gln Ser Cys Leu Lys Phe Lys Ala Asn
385                 390                 395                 400

Asp His Gly Tyr Asp Asn Phe Arg Ser Ser Asn Lys Tyr Ser Ser Ser
                405                 410                 415

<210> SEQ ID NO 12
<211> LENGTH: 10
<212> TYPE: PRT
<213> ORGANISM: Artificial sequence
<220> FEATURE:
<223> OTHER INFORMATION: Synthetic

<400> SEQUENCE: 12

Gly Tyr Thr Phe Thr Ser Tyr Trp Met Gln
1               5                   10

<210> SEQ ID NO 13
<211> LENGTH: 17
<212> TYPE: PRT
<213> ORGANISM: Artificial sequence
<220> FEATURE:
<223> OTHER INFORMATION: Synthetic

<400> SEQUENCE: 13
```

Thr Ile Tyr Pro Gly Asp Gly Asp Thr Ser Tyr Ala Gln Lys Phe Lys
1               5                   10                  15

Gly

<210> SEQ ID NO 14
<211> LENGTH: 9
<212> TYPE: PRT
<213> ORGANISM: Artificial sequence
<220> FEATURE:
<223> OTHER INFORMATION: Synthetic

<400> SEQUENCE: 14

Trp Gly Tyr Ala Tyr Asp Ile Asp Asn
1               5

<210> SEQ ID NO 15
<211> LENGTH: 16
<212> TYPE: PRT
<213> ORGANISM: Artificial sequence
<220> FEATURE:
<223> OTHER INFORMATION: Synthetic

<400> SEQUENCE: 15

Lys Ser Ser Gln Ser Leu Leu Asp Ser Asp Gly Lys Thr Tyr Leu Asn
1               5                   10                  15

<210> SEQ ID NO 16
<211> LENGTH: 7
<212> TYPE: PRT
<213> ORGANISM: Artificial sequence
<220> FEATURE:
<223> OTHER INFORMATION: Synthetic

<400> SEQUENCE: 16

Leu Val Ser Lys Leu Asp Ser
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic

<400> SEQUENCE: 17

Trp Gln Gly Thr His Phe Pro Tyr Thr
1               5

<210> SEQ ID NO 18
<211> LENGTH: 219
<212> TYPE: PRT
<213> ORGANISM: Artificial sequence
<220> FEATURE:
<223> OTHER INFORMATION: Synthetic

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Asp Gly Lys Thr Tyr Leu Asn Trp Leu Gln Gln Lys Pro Gly Lys Ala
        35                  40                  45

Pro Lys Arg Leu Ile Tyr Leu Val Ser Lys Leu Asp Ser Gly Val Pro
    50                  55                  60

```
Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Trp Gln Gly
                 85                  90                  95

Thr His Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Cys Thr Lys Ser Phe Asn Arg Gly Glu Cys
    210                 215

<210> SEQ ID NO 19
<211> LENGTH: 448
<212> TYPE: PRT
<213> ORGANISM: Artificial sequence
<220> FEATURE:
<223> OTHER INFORMATION: Synthetic

<400> SEQUENCE: 19

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Tyr
                 20                  25                  30

Trp Met Gln Trp Val Arg Gln Ala Pro Gly Lys Gly Leu Glu Trp Ile
             35                  40                  45

Gly Thr Ile Tyr Pro Gly Asp Gly Asp Thr Ser Tyr Ala Gln Lys Phe
     50                  55                  60

Lys Gly Arg Ala Thr Leu Ser Thr Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Gly Tyr Ala Tyr Asp Ile Asp Asn Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 20
<211> LENGTH: 448
<212> TYPE: PRT
<213> ORGANISM: Artificial sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Ser Tyr
            20                  25                  30
Trp Met Gln Trp Val Arg Gln Ala Pro Gly Lys Gly Leu Glu Trp Ile
        35                  40                  45
Gly Thr Ile Tyr Pro Gly Asp Gly Asp Thr Ser Tyr Ala Gln Lys Phe
    50                  55                  60
Lys Gly Arg Ala Thr Leu Ser Thr Asp Lys Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Trp Gly Tyr Ala Tyr Asp Ile Asp Asn Trp Gly Gln Gly Thr
            100                 105                 110
Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Cys Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 21
<211> LENGTH: 10
<212> TYPE: PRT
<213> ORGANISM: Artificial sequence
<220> FEATURE:
<223> OTHER INFORMATION: Synthetic

<400> SEQUENCE: 21

Gly Tyr Ser Phe Thr Arg Tyr Thr Met Asn
1               5                   10

<210> SEQ ID NO 22
<211> LENGTH: 17
<212> TYPE: PRT
<213> ORGANISM: Artificial sequence
<220> FEATURE:
```

-continued

<223> OTHER INFORMATION: Synthetic

<400> SEQUENCE: 22

Val Ile Asn Pro Tyr Asn Gly Gly Thr Val Tyr Asn Gln Lys Phe Lys
1               5                   10                  15

Gly

<210> SEQ ID NO 23
<211> LENGTH: 10
<212> TYPE: PRT
<213> ORGANISM: Artificial sequence
<220> FEATURE:
<223> OTHER INFORMATION: Synthetic

<400> SEQUENCE: 23

Thr Asp Tyr Asp Gly Tyr Ala Met Asp Tyr
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic

<400> SEQUENCE: 24

Ser Gly Ser Thr Leu Gln Ser
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic

<400> SEQUENCE: 25

Gln Gln His Asn Glu Tyr Pro Tyr Thr
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic

<400> SEQUENCE: 26

Ser Gly Ser Thr Leu Gln Ser
1               5

<210> SEQ ID NO 27
<211> LENGTH: 219
<212> TYPE: PRT
<213> ORGANISM: Artificial sequence
<220> FEATURE:
<223> OTHER INFORMATION: Synthetic

<400> SEQUENCE: 27

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

```
Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
 65                  70                  75                  80

Thr Arg Val Glu Ala Glu Asp Leu Gly Val Tyr Tyr Cys Trp Gln Gly
                 85                  90                  95

Thr His Phe Pro Tyr Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 28
<211> LENGTH: 448
<212> TYPE: PRT
<213> ORGANISM: Artificial sequence
<220> FEATURE:
<223> OTHER INFORMATION: Synthetic

<400> SEQUENCE: 28

```
Gln Val Gln Leu Leu Gln Ser Gly Ala Glu Leu Ala Arg Pro Gly Ala
  1               5                  10                  15

Ser Val Lys Leu Ser Cys Lys Ala Ser Gly Tyr Thr Phe Thr Ser Tyr
                 20                  25                  30

Trp Met Gln Trp Val Lys Gln Arg Pro Gly Gln Gly Leu Glu Trp Ile
             35                  40                  45

Gly Thr Ile Tyr Pro Gly Asp Gly Asp Thr Ser Tyr Ala Gln Lys Phe
         50                  55                  60

Lys Gly Lys Ala Thr Leu Thr Thr Asp Lys Ser Ser Thr Ala Tyr
 65                  70                  75                  80

Met Gln Leu Ser Ser Leu Ala Ser Glu Asp Ser Ala Val Tyr Tyr Cys
                 85                  90                  95

Ala Arg Trp Gly Tyr Ala Tyr Asp Ile Asp Asn Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190
```

```
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
        435                 440                 445
```